United States Patent [19]
Wong et al.

[11] Patent Number: 5,830,871
[45] Date of Patent: Nov. 3, 1998

[54] INHIBITORS OF E-, P- AND L-SELECTIN BINDING

[75] Inventors: Chi-Huey Wong, Rancho Santa Fe; Francisco Moris-Varas, San Diego; Chun-Cheng Lin, La Mesa, all of Calif.

[73] Assignee: The Scripps Research Institute, La Jolla, Calif.

[21] Appl. No.: 744,744

[22] Filed: Oct. 28, 1996

[51] Int. Cl.$^6$ .............................. A61K 31/70; C12P 19/02
[52] U.S. Cl. .......................... 514/23; 514/459; 514/460; 435/105; 435/125; 536/17.2; 536/117; 549/222
[58] Field of Search ................................. 435/105, 125; 514/23, 459, 460; 536/17.2, 117; 549/222

[56] References Cited

U.S. PATENT DOCUMENTS

| | | | |
|---|---|---|---|
| 4,785,330 | 11/1988 | Furie et al. | 424/1.53 |
| 5,079,353 | 1/1992 | Ratcliffe et al. | 536/53 |
| 5,163,712 | 11/1992 | Brandley et al. | 424/1.73 |
| 5,296,594 | 3/1994 | Ratcliffe et al. | 536/53 |
| 5,519,008 | 5/1996 | Rao et al. | 514/26 |
| 5,527,785 | 6/1996 | Bevilaqua et al. | 514/56 |

FOREIGN PATENT DOCUMENTS

| | | |
|---|---|---|
| WO/91/19501 | 12/1991 | WIPO . |
| WO/91/19502 | 12/1991 | WIPO . |
| 92/22564 | 12/1992 | WIPO . |

OTHER PUBLICATIONS

DeFrees, et al. J. Am. Chem. Soc., 117:66–79 (1995).
Allanson, et al., Tetrehedron Lett, 34:3945 (1993).
Ragan, et al. Bioorg. Med. Chem. Lett., 4: 2563 (1994).
Hanessian, et al. Synlett, 868 (1994).
Huang, et al., J. Org. Chem. 1995 60, 3100.
Prodger, et al. Tetrahedron Lett. 1995, 36, 2339.
Marasinga rao, J. Biol. Chem. 1994, 269, 1963.
Uchiyama, et al., J. Am. Chem. Soc. 1995, 117, 5395.

*Primary Examiner*—Kathleen K. Fonda
*Attorney, Agent, or Firm*—Donald G. Lewis

[57] ABSTRACT

Inhibitors of E-, P- and L-selectin binding are synthesized by an aldol addition reaction between a glycoside aldehyde precursor and dihydroxyacetone phosphate or a derivative thereof. The addition reaction is catalyzed by aldolase. The inhibitors exhibit an activity comparable to sialyl Lewis X with respect to the E-selectin binding assay and high activities in the P- and L-selectin binding assays. The inhibitors are employable for blocking neutrophil inflamatory conditions.

42 Claims, 13 Drawing Sheets

Biological Data for compound 6

(correlates to class II compound figure 1 wherein R=OH):

E-Selectin  $IC_{50} = 0.8$ mM

P-Selectin  >80% inhib. @ 3 mM

L-Selectin  >80% inhib. @ 3 mM

| Name | 6 | 13 | 7 |
|---|---|---|---|
| H1 | 4.20 (ddd)<br>$J_{H1,H1'a} = 11.5$<br>$J_{H1,H1'b} = 3.6$<br>$J_{H1,H2} = 2$ | 4.12 (ddd)<br>$J_{H1,H1'a} = 10$<br>$J_{H1,H1'b} = 3.5$<br>$J_{H1,H2} = 6$ | 4.15 (ddd)<br>$J_{H1,H1'a} = 11$<br>$J_{H1,H1'b} = 3.5$<br>$J_{H1,H2} = 3.3$ |
| H2 | 3.77 (dd)<br>$J_{H2,H3} = 3.3$<br>$J_{H2,H1} = 2$ | 3.60 (dd)<br>$J_{H2,H3} = 10$<br>$J_{H2,H1} = 6$ | 3.73 (dd)<br>$J_{H2,H3} = 2.3$<br>$J_{H2,H1} = 3.3$ |
| H3 | 3.67 (dd)<br>$J_{H3,H2} = 3.3$<br>$J_{H3,H4} = 9.3$ | 3.52 (t)<br>$J_{H4,H3} = J_{H4,H5} = 10$ | 3.65 (dd)<br>$J_{H3,H2} = 2.3$<br>$J_{H3,H4} = 9.4$ |
| H4 | 3.48 (t)<br>$J_{H4,H3} = J_{H4,H5} = 9.3$ | 3.21 (t)<br>$J_{H4,H3} = J_{H4,H5} = 10$ | 3.49 (t)<br>$J_{H4,H3} = J_{H4,H5} = 9.4$ |
| H5 | 3.42 (ddd)<br>$J_{H5,H4} = 9.3$<br>$J_{H5,H6a} = 2.2$<br>$J_{H5,H6b} = 5.8$ | 3.42 (ddd)<br>$J_{H5,H4} = 10$<br>$J_{H5,H6a} = 2$<br>$J_{H5,H6b} = 6$ | 3.42 (ddd)<br>$J_{H5,H4} = 9.4$<br>$J_{H5,H6a} = 4.4$<br>$J_{H5,H6b} = 5.8$ |
| H6a | 3.74 (dd)<br>$J_{H6a,H6b} = 12.1$<br>$J_{H6a,H5} = 2.2$ | 3.72 (dd)<br>$J_{H6a,H6b} = 12$<br>$J_{H6a,H5} = 2$ | 3.79 (dd)<br>$J_{H6a,H6b} = 12.3$<br>$J_{H6a,H5} = 4.4$ |
| H6b | 3.56 (dd)<br>$J_{H6b,H6a} = 12.1$<br>$J_{H6b,H5} = 5.8$ | 3.56 (dd)<br>$J_{H6b,H6a} = 12$<br>$J_{H6b,H5} = 6$ | 3.58 (dd)<br>$J_{H6b,H6a} = 12.3$<br>$J_{H6b,H5} = 5.8$ |

| | | | |
|---|---|---|---|
| H1'a | 1.92 (ddd) $J_{H1'a,H1'b} = 14.7$ $J_{H1'a,H1} = 11.5$ $J_{H1'a,H2'} = 3$ | 1.8 (ddd) $J_{H1'a,H1'b} = 14$ $J_{H1'a,H1} = 10$ $J_{H1'a,H2'} = 3.5$ | 2.10 (ddd) $J_{H1'a,H1'b} = 14.2$ $J_{H1'a,H1} = 11$ $J_{H1'a,H2'} = 3$ |
| H1'b | 1.60 (ddd) $J_{H1'b,H1'a} = 14.7$ $J_{H1'b,H2'} = 10.4$ $J_{H1'b,H1} = 3.6$ | Same as H1'a | 1.75 (ddd) $J_{H1'b,H1'a} = 14.2$ $J_{H1'b,H2'} = 10$ $J_{H1'b,H1} = 3.5$ |
| H2' | 4.28 (ddd) $J_{H2',H1'b} = 10.4$ $J_{H2',H1'a} = 3$ $J_{H2',H3'} = 2$ | 4.06 (ddd) $J_{H2',H1'b} = 10$ $J_{H2',H1'a} = 3.5$ $J_{H2',H3'} = 2$ | 4.29 (ddd) $J_{H2',H1'b} = 10$ $J_{H2',H1'a} = 3$ $J_{H2',H3'} = 2$ |
| H3' | 4.33 (d) $J_{H3',H2'} = 2$ | 4.37 (d) $J_{H3',H2'} = 2$ | 4.39 (d) $J_{H3',H2'} = 2$ |
| H4' | na | na | na |
| H5'a | 4.45 (dd) $J_{H5'a,H5'b} = 18.7$ $^3J_{H5'a,P} = 6$ | 4.48 (dd) $J_{H5'a,H5'b} = 18.7$ $^3J_{H5'a,P} = 6.2$ | 2.82 (m) (H5'a + H5'b) |
| H5'b | 4.55 (dd) $J_{H5'b,H5'a} = 18.7$ $^3J_{H5'b,P} = 6$ | 4.58 (dd) $J_{H5'b,H5'a} = 18.7$ $^3J_{H5'b,P} = 6.2$ | 1.60 (m) (H6'a + H6'b) |

| Aldolase: Sugar: | 6 | 13 | 7 |
|---|---|---|---|
| C1 | 75.11 | 75.67 | 76.91 |
| C2 | 70.86* | 75.31* | 71.38* |
| C3 | 72.09* | 74.66* | 71.88* |
| C4 | 67.65* | 73.29* | 63.51* |
| C5 | 73.97 | 73.01* | 75.00 |
| C6 | 61.47 | 63.66 | 61.94 |
| C1' | 30.49 | 29.71 | 32.47 |
| C2' | 68.20* | 69.78 | 67.73* |
| C3' | 78.13 | 80.49 | 78.34 |
| C4' | 212.60 $^3J_{C,P} = 15$ | 213.50 $^3J_{C,P} = 16$ | 213.8 $^3J_{C,P} = 15$ |
| C5' | 68.40 $^2J_{C,P}$ = nd | 70.60 $^2J_{C,P} = 4$ | 34.15 $^2J_{C,P}$ = nd |
| C6' | na | na | 25.72 $^1J_{C,P} = 138$ |

\* Tentative Assignment.
nd= not determined.
na=not applicable

FIG. 10

INHIBITORS OF E-, P- AND L-SELECTIN BINDING

GOVERNMENT RIGHTS

This invention was made with government support under Grant No. GM 44154 awarded by the National Institutes of Health. The U.S. government has certain rights in the invention.

SPECIFICATION

1. Technical Field

The present invention relates to compounds that inhibit cellular adhesion. More particularly, the present invention relates to E-, P- and L-Selectin inhibitors and to enzymatic aldol addition reactions for synthesizing such inhibitors.

2. Background

The term "selectin" is employed to designate a general class of receptor which displays a selective adhesive function and which includes a lectin-like domain responsible for such selective adhesive function. Known selectings include E-selectin, P-selectin, and L-selectin. E-selectin corresponds to glycoprotein ELAM-1 (endothelial leukocyte adhesion molecule-1); P-selectin corresponds to glcyoprotein GMP-140 (granule membrane protein-140); and L-selectin corresponds to glycoprotein MEL-14. The structure and function of each of these selectin receptors has been elucidated by cloning and expression of full length cDNA encoding each of the above receptors.

The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263:9557–9560 (1988) that induces low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

E-selectin is a cell surface protein inducibly expressed in endothelial cells in response to inflammatory factors. Inflammatory factors which induce E-selectin include interleukin Iβ (IL-Iβ), tumor necrosis factor α (TNFα), leukotriene $B_4$ neurotoxins, and various lipopolysaccharide bacterial endotoxins. Each of these compounds induces the expression of E-selectin in endothelial cells and platelets and augments their adhesion properties. Specifically, expression of E-selectin is associated with the binding of endothelial cells and platelets to human polymorphonuclear leukocytes (neutrophils), monocytes, eosinophils, certain T-lymphocytes, NK cells, and the promyelocytic cell line HL-60. For example, binding of neutrophils to endothelial cells is observed at an early stage after tissue injury and is associated with various acute and chronic inflammations.

Sialyl Lewis X ($SLe^x$) mediates binding of neutrophils to vascular endothelial cells by binding to E-selectin. (M. Phillips, et al., . *Science.* 1990, 250, 1130.; J. Lowe, et al, *Cell.* 1990, 63, 475; T. Feizi, *Trends. Biochem. Sci.* 1991, 16, 84; M. Tiemeyer., et al., *Proc. Natl. Acad. Sci. U.S.A.* 1991, 88, 1138; L. Lasky. *Science.* 1992, 258, 964; and T. Springer, L. A. Lasky, *Nature* 1991, 349, 196.) Sialyl Lewis X ($SLe^x$) is a cell surface carbohydrate ligand found on neutrophils, anchored onto the outer membrane thereof by integral membrane glycoproteins and/or glycolipids. Administration of $SLe^x$ inhibits the $SLe^x$/E-selectin interaction and blocks adhesion of neutophils to endothelial cells. (M. Buerke, et al., *J. Clin. Invest.,* 1994, 1140.). Neutrophil-mediated inflammatory diseases may be treated by administration of Sialyl Lewis X ($SLe^x$).

In addition to binding to neutrophils, vascular endothelial cells play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

P-selectin (also known as GMP-140 and PADGEM) is present on the surface of platelets and endothelial cells, where it mediates platelet-leukocyte and endothelium-leukocyte interactions. Thus, for example, activated platelets that express P-selectin on their surface are known to bind to monocytes and neutrophils, and also to bind monocyte-like cell lines, e.g., HL-60 and U937.

P-selectin is an alpha granule membrane protein of molecular mass 140,000 that is expressed on the surface of activated platelets upon platelet stimulation and granule secretion. It is also found in megakaryocytes within the Weibel-Palade bodies. Furie et al., U.S. Pat. No. 4,783,330, describe monoclonal antibodies reactive with P-selectin.

A third receptor is the lymphocyte homing receptor, MEL-14 antigen or its human counterpart LAM-1 (L-selectin). In addition to lymphocyte homing, MEL-14 antigen/LAM-1 is believed to function early in neutrophil binding to the endothelium.

U.S. Pat. No. 5,079,353 and its divisional U.S. Pat. No. 5,296,594 teach the synthesis and use of the sialyl Lewis X (sialyl $Le^x$ or $SLe^x$) and sialyl Lewis A (sialyl $Le^a$ or $Sle^a$) antigens that are present in cancerous tissues, and are ligands for the before-described selectin receptors. U.S. Pat. No. 5,143,712 teaches the binding interactions between various receptors such as ELAM-1 (E-selectin) and ligands such as sialyl $Le^x$ as well as ligands containing a plurality of N-acetyllactosamine (LacNAc) units along with a terminal sialyl group and one or more fucosyl groups that are bonded to the GlcNAc portion of a LacNAc unit.

Published International application WO 91/19501 and WO 91/19502 disclose that oligosaccharides containing the pentameric and hexameric structures shown below inhibited selective cellular binding between cells containing the ligand (below) and those containing a selectin receptor, and that the penta- and hexasaccharides assayed provided better inhibition than did SLe$^x$.

NeuAcα2→3Galβ1→4(Fucα1→3)GlcNAcβ1, 3Galβ-;

NeuAcα2→3Galβ1→4(Fucα1→3)GlcNAcβ1, 3Galβ1, 4Glc-; and

NeuAcα2→3Galβ1→4(Fucα1→3GlcNAc=Sle$^x$.

Mulligan et al., Nature, 364; 149–151 (1993) reported upon the in vivo effects of Sle$^x$ and a pentamer such as that above present as a —O(CH$_2$)$_5$CO$_2$CH$_3$ glycoside in a neutrophil/P-selection-dependent rat model. Those authors found that intravenous infusion of up to 200 μg of SLe$^x$ or the pentamer dramatically reduced lung injury and diminished tissue accumulation of neutrophils in rats that received an intravenous infusion of cobra venom. Based on the concentrations used, 200 μg, the effective intravenous concentration of SLe$^x$ was calculated to be less than 1 μM.

DeFrees et al., J. Am. Chem. Soc.,117:66–79 (1995) reported on the in vitro inhibition of binding between E-selectin and SLe$^x$-bearing HL-60 cells for a number of SLe$^x$-related materials including SLe$^x$ itself, an ethyl glycoside of the above pentamer and a number of bivalent SLe$^x$ analogs. Those authors noted that although the affinity of SLe$^x$ for E-selectin is relatively weak in vitro, the IC$_{50}$ value in vivo for protecting against lung injury in rats was in the 1 μM range.

Although SLe$^x$ has been considered to be potentially useful as anti-inflammatory agent and its synthesis on large scales has been developed for clinical evaluation, this natural saccharide can only be used as an injectable form in cases presenting with acute symptoms as it is orally inactive and unstable in the blood stream, because of glycosidase reductions.

The search for novel SLe$^x$ mimetics with simpler structure, higher affinity for the receptor, and better stability against glycosidases, especially fucosidase and sialidase, has been of current interest. A SLe$^x$ mimetic is a compound which includes the functional groups of SLe$^x$ and which mimics the active conformation of SLe$^x$ in space, but which lacks one or more of the glycosidic bonds of SLe$^x$ and/or one or more of the saccharide subunits or analogs thereof. Several active SLe$^x$ mimetics and SLe$^x$ analogs have been designed and synthesized, e.g., a) Allanson, et al., Tetrahedron Lett, 34:3945 (1993), 3945 (30-fold less active than SLe$^x$); b) Ragan, et al., Bioorg. Med. Chem. Lett, 4:2563 (1994) (a mixture of 4 diastereomers with 40- to 50-fold less activity); c) Hanessian, et al., Synlett, 868 (1993) (inactive); and d)H. Huang and C.-H. Wong. J. Org. Chem. 1995, 60, 3100; J. C. Prodger, et al. Tetrahedron Lett. 1995, 36, 2339; and B. N. Narasinga Rao,. J. Biol. Chem. 1994, 269, 19663. Two SLe$^x$ mimetics synthesized by Uchiyama et al. are of particular note because they exhibit activities similar to SLe$^x$ in the E-selectin binding assay. (T. Uchiyama, et al.. J. Am. Chem. Soc. 1995, 117, 5395.) For active natural products inhibiting E-selectin, see Narasinga Rao, et al., J. Biol. Chem., 269:19663 (1994).

The key structural features of SLe$^x$ required for recognition by E-selectin have been determined by structural and conformational studies and by comparative studies of the blocking activity of SLe$^x$ analog families.. (B.Brandley, Glycobiology 1993, 3, 633; S. DeFrees, J. Am. Chem. Soc. 1993, 115, 7549; J. Ramphal, J. Med. Chem. 1994, 37, 3459; D. Tyrrell, Proc. Natl. Acad. Sci. USA 1991, 88, 10372; R.Nelson,. J. Clin. Invest. 1993, 91, 1157; and A. Giannis, Angew. Chem. Int. Ed. Engl. 1994. 33. 178.) The solution conformation of SLe$^x$ has been characterized using physical methodologies. (Y. C. Lin, et al., J. Am. Chem. Soc. 1992, 114, 5452; Y. Ichikawa, et al.. J. Am. Chem. Soc., 1992, 114, 9283; and G. E. Ball et al., J. Am. Chem. Soc., 1992, 114, 5449.) The three-dimensional structure of the human E-selectin has been characterized by X-ray diffraction. (B. J. Graves, et al.,. Nature, 1994, 367, 532.) It has been found that the L-fucose, D-galactose (Gal) and sialic acid moieties of SLe$^x$ are the major components that interact with E-selectin. N-acetylglucosamine unit appears to act merely as a linker to connect L-fucose and sialyl galactose. The six functional groups of SLe$^x$ molecule including the 2-, 3- and 4-OH groups of L-fucose, the 4- and 6—OH groups of Gal and the —CO$_2^-$- group of sialic acid are essential for E-selectin recognition.

Although SLe$^x$ and active SLe$^x$ analogs can be employed as anti-inflammatory agents, these tetrasaccharides can only be used in acute symptoms as they are unstable in the blood and orally inactive. In addition, it is generally difficult to synthesize oligosaccharides on a large-scale. The use of SLe$^x$ mimetics can obviate the above problems associated with SLe$^x$ analogs. Unfortunately, SLe$^x$ mimetics generally have low activity.

What are needed are SLe$^x$ mimetics which are more stable as compared to SLe$^x$ and SLe$^x$ analogs; which possess better bioavailability as compared to SLe$^x$ and SLe$^x$ analogs; which are easier to synthesize than SLe$^x$ and SLe$^x$ analogs; and which exhibit greater activity as compared to known SLe$^x$ mimetics.

SUMMARY

One aspect of the invention is directed to inhibitors of E-, P- and L- selectin binding wherein the inhibitors are represented by the following formulas:

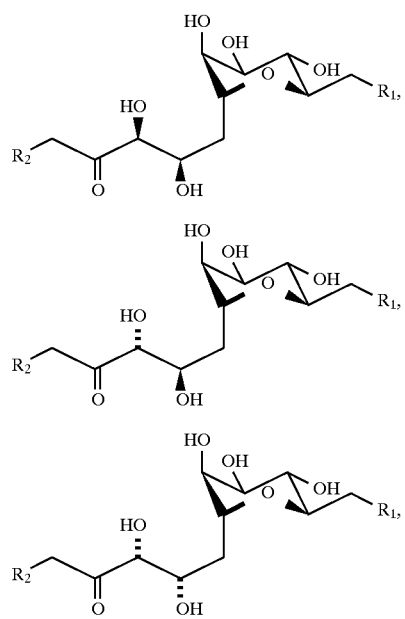

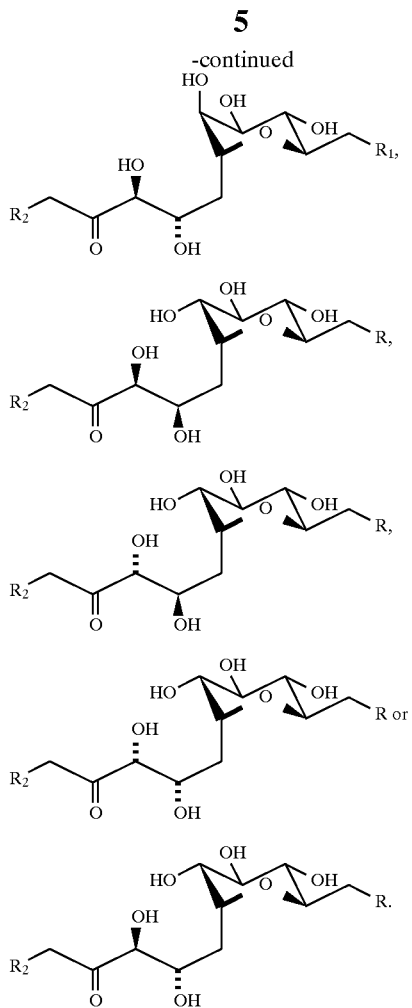

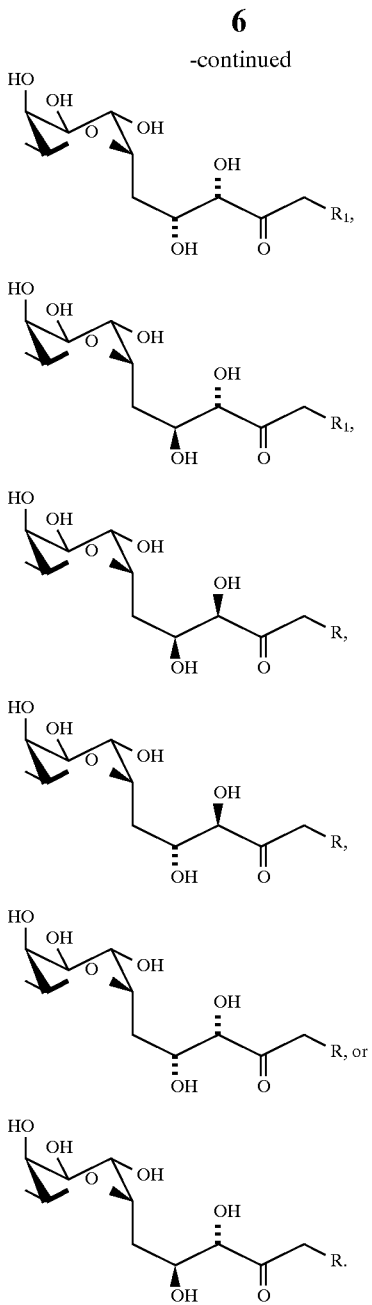

In the above formulas, $R_1$ is a radical selected from the group consisting of —H, —OH, —O—$C_1$—$C_6$, —OBn, —$N_3$, —$OSO_3^{2-}$, —$OCOCH_2CH_2CONHCH(CH_2CO_2H)CO_2H$, and —NHR'. R' is a radical selected from the group consisting of alkyl ($C_1$-$_{C6}$), acyl, decanoyl, phenylacetyl, and —$COCH_2CH_2CO_2H$. $R_2$ is a radical selected from the group consisting of —$CH_2PO_3^{2-}$ and —$OPO_3^{2-}$.

Another aspect of the invention is directed to inhibitors of E-, P- and L- selectin binding wherein the inhibitors are represented by the following formulas:

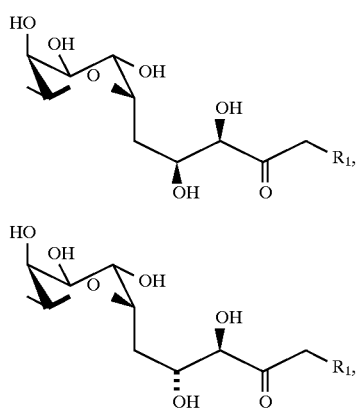

In the above formulas, $R_1$ is a radical selected from the group consisting of —$CH_2PO_3^{2-}$ and —$OPO_3^{2-}$.

Another aspect of the invention is directed to inhibitors of E-, P- and L- selectin binding wherein the inhibitors are represented by the following formulas:

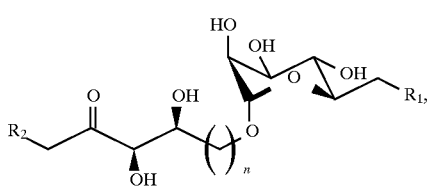

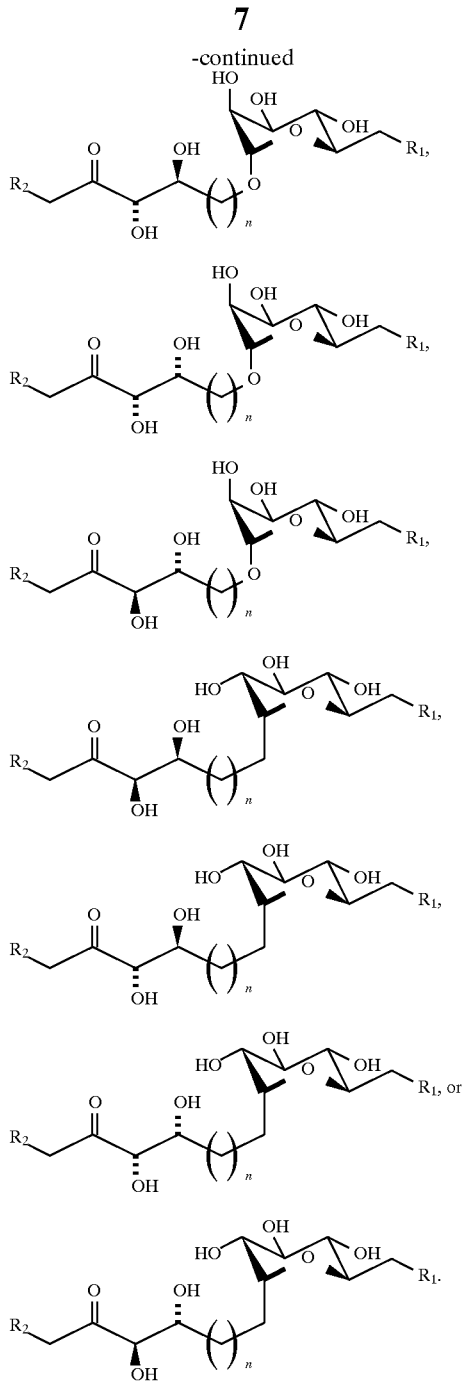

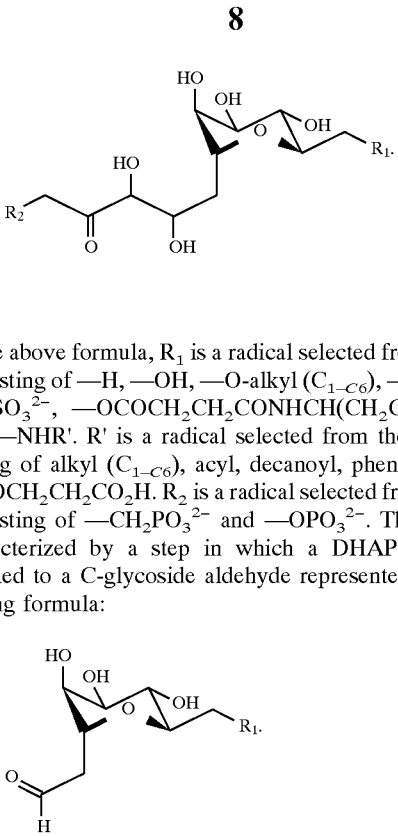

In the above formula, $R_1$ is a radical selected from the group consisting of —H, —OH, —O-alkyl ($C_{1-C6}$), —OBn, —$N_3$, —$OSO_3^{2-}$, —$OCOCH_2CH_2CONHCH(CH_2CO_2H)CO_2H$, and —NHR'. R' is a radical selected from the group consisting of alkyl ($C_{1-C6}$), acyl, decanoyl, phenylacetyl, and —$COCH_2CH_2CO_2H$. $R_2$ is a radical selected from the group consisting of —$CH_2PO_3^{2-}$ and —$OPO_3^{2-}$. The method is characterized by a step in which a DHAP substrate is coupled to a C-glycoside aldehyde represented by the following formula:

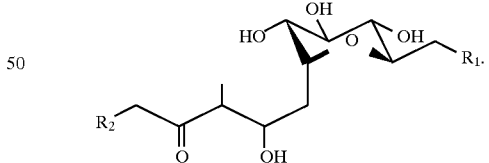

The coupling step is catalyzed by a DHAP dependent aldolase for producing the E-, P- and L- selectin inhibitor. In a preferred mode, the DHAP substrate is a compound selected from the group consisting of dihydroxyacetone phosphate and 3-keto-4-hydroxy-butanyl-1-phosphonate. In an alternative preferred modes, the DHAP dependent aldolase is selected from the group consisting of FDPA, FucA, RhaA and TagA.

Another aspect of the invention is directed to methods for synthesizing an E-, P- and L- selectin inhibitor represented by the formula:

In the above formulas, $R_1$ is a radical selected from the group consisting of —H, —OH, —O-alkyl ($C_{1-C6}$), —OBn, —$N_3$, —$OSO3^{2-}$, —$OCOCH_2CH_2CONHCH(CH_2CO_2H)CO_2H$, and —NHR'. R' is a radical selected from the group consisting of alkyl ($C_{1-C6}$), acyl, decanoyl, phenylacetyl, and —$COCH_2CH_2CO_2H$. $R_2$ is a radical selected from the group consisting of —$CH_2PO_3^{2-}$ and $OPO_3^{2-}$. "n" runs from 1 to 4.

Another aspect of the invention is directed to methods for synthesizing an E-, P- and L- selectin inhibitor represented by the formula:

In the above formula, $R_1$ is a radical selected from the group consisting of —H, —OH, —O-alkyl($C_{1-C6}$), —OBn, —$N_3$, —$OSO_3^{2-}$, —$OCOCH_2CH_2CONHCH(CH_2CO_2H)CO_2H$, and —NHR'. R' is a radical selected from the group consisting of alkyl ($C_1$–$C_6$), acyl, decanoyl, phenylacetyl, and —$COCH_2CH_2CO_2H$. $R_2$ is a radical selected from the group consisting of —$CH_2PO_3^2$ and $OPO_3^{2-}$. The method is characterized by a step in which a DHAP substrate is coupled to a C-glycoside aldehyde represented by the following formula:

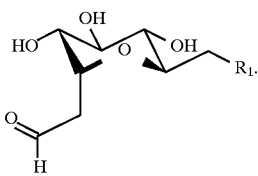

The coupling step is catalyzed by a DHAP dependent aldolase for producing the E-, P- and L- selectin inhibitor. In a preferred mode, the DHAP substrate is a compound selected from the group consisting of dihydroxyacetone phosphate and 3-keto-4-hydroxy-butanyl-1-phosphonate. In an alternative preferred modes, the DHAP dependent aldolase is selected from the group consisting of FDPA, FucA, RhaA and TagA.

Another aspect of the invention is directed to methods for synthesizing an E-, P- and L- selectin inhibitor represented by the formula:

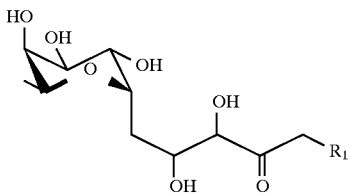

In the above formula, $R_1$ is a radical selected from the group consisting of $-CH_2PO_3^{2-}$ and $OPO_3^{2}$. The method is characterized by a step in which a DHAP substrate is coupled to a C-glycoside aldehyde represented by the following formula:

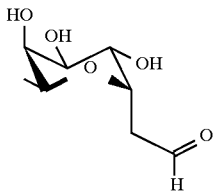

The coupling step is catalyzed by a DHAP dependent aldolase for producing the E-, P- and L- selectin inhibitor. In a preferred mode, the DHAP substrate is a compound selected from the group consisting of dihydroxyacetone phosphate and 3-keto-4-hydroxy-butanyl-1-phosphonate. In an alternative preferred modes, the DHAP dependent aldolase is selected from the group consisting of FDPA, FucA, RhaA and TagA.

Another aspect of the invention is directed to methods for synthesizing an E-, P- and L- selectin inhibitor represented by the formula:

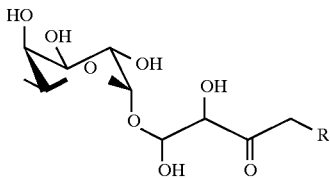

In the above formula, $R_1$ is a radical selected from the group consisting of $-CH_2PO_3^{2-}$ and $-OPO_3^{2-}$. The method is characterized by a step in which a DRAP substrate is coupled to an O-glycoside aldehyde represented by the following formula:

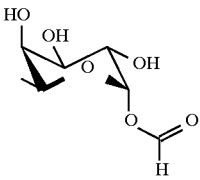

The coupling step is catalyzed by a DHAP dependent aldolase for producing the E-, P- and L- selectin inhibitor. In a preferred mode, the DHAP substrate is a compound selected from the group consisting of dihydroxyacetone phosphate and 3-keto-4-hydroxy-butanyl-1-phosphonate. In an alternative preferred modes, the DHAP dependent aldolase is selected from the group consisting of FDPA, FucA, RhaA and TagA.

Another aspect of the invention is directed to methods for synthesizing an E-, P- and L- selectin inhibitor represented by the formula:

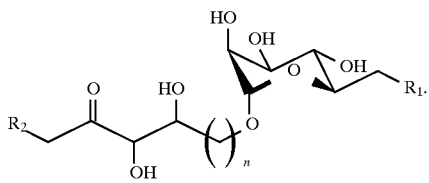

In the above formula, $R_1$ is a radical selected from the group consisting of $-H$, $-OH$, $-O$-alkyl $(C_1-C_6)$, $-OBn$, $-N_3$, $-OSO_3^{2-}$, $-OCOCH_2CH_2CONHCH(CH_2CO_2H)CO_2H$, and $-NHR'$. $R'$ is a radical selected from the group consisting of alkyl$(C_{1-C6})$, acyl, decanoyl, phenylacetyl, and $-COCH_2CH_2CO_2H$. $R_2$ is a radical selected from the group consisting of $-CH_2PO_3^{2-}$ and $-OPO_3^{2-}$. "n" runs from 1 to 4. The method is characterized by a step in which a DHAP substrate is coupled to an 0-glycoside aldehyde represented by the following formula:

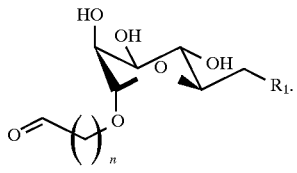

The coupling step is catalyzed by a DHAP dependent aldolase for producing the E-, P- and L- selectin inhibitor. In a preferred mode, the DHAP substrate is a compound selected from the group consisting of dihydroxyacetone phosphate and 3-keto-4-hydroxy-butanyl-1-phosphonate. In an alternative preferred modes, the DHAP dependent aldolase is selected from the group consisting of FDPA, FucA, RhaA and TagA.

Another aspect of the invention is directed to methods for synthesizing an E-, P- and L- selectin inhibitor represented by the formula:

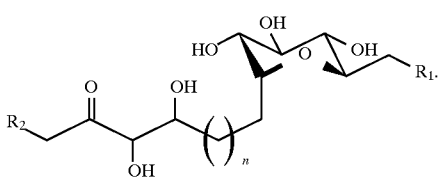

In the above formula, $R_1$ is a radical selected from the group consisting of —H, —OH, —O-alkyl($C_{1-C6}$), —OBn, —$N_3$, —$OSO_3^{2-}$, —$OCOCH_2CH_2CONHCH(CH_2CO_2H)CO_2H$, and —NHR'. R' is a radical selected from the group consisting of alkyl ($C_{1-C6}$), acyl, decanoyl, phenylacetyl, and —$COCH_2CH_2CO_2H$. $R_2$ is a radical selected from the group consisting of —$CH_2PO_3^{2-}$ and —$OPO_3^{2-}$. "n" runs from 1 to 4. The method is characterized by a step in which a DHAP substrate is coupled to an O-glycoside aldehyde represented by the following formula:

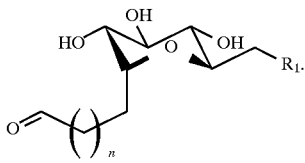

The coupling step is catalyzed by a DHAP dependent aldolase for producing the E-, P- and L- selectin inhibitor. In a preferred mode, the DHAP substrate is a compound selected from the group consisting of dihydroxyacetone phosphate and 3-keto-4-hydroxy-butanyl-1-phosphonate. In an alternative preferred modes, the DHAP dependent aldolase is selected from the group consisting of FDPA, FucA, RhaA and TagA.

DESCRIPTION OF FIGURES

FIG. 9 illustrates the indicated $^1$H-NMR Data for C-Glycoside Phosphates and Phosphonates Prepared Enzymatically.

FIG. 10 illustrates the indicated $^{13}$C-NMR Data for C-Glycoside phosphates and phosphonates prepared enzymatically.

DETAILED DESCRIPTION OF THE INVENTION

The invention is directed to the design and synthesis of novel E-, P- and L- Selectin inhibitors, based on combinatorial enzymatic aldol addition reactions. The claimed compounds include C-glycoside phosphates, 0-glycoside phosphates, C-glycoside phosphonates and O-glycoside phosphonates and are based on L-fucose, D-glucose and D-mannose templates. The methodology involves the coupling of dihydroxyacetone phosphate (DHAP) or phosphonate analogs of DHAP to a glycoside based aldehyde using an aldolase to form the selectin inhibitor or a library of inhibitors thereof. Different aldolases achieve different stereochemistries; some of the suggested aldolases include FDPA, FucA, RhaA and TagA.

Compound 6 is one of the preferred compounds of the invention. It contains a D-mannose sugar template with a side chain which contains a phosphate moiety (=$O_3PO$) derived from DHAP, and two hydroxyl groups wherein one hydroxyl moiety is derived from DHAP and the other hydroxyl moiety is derived from the conversion of the C-glycoside aldehyde moiety to an alcohol upon aldol addition of DHAP with the C-glycoside aldehyde using FDPA aldolase. The two OH groups mimic the 4- and 6-OH groups of the Gal residue of the sialic acid residue and the phosphate mimics the negative charge of the sialic acid residue. Compound 7 was designed in a similar way to compound 6, except that the phosphate group was replaced with a phosphonate moiety in order to assess further activity with potential increased stability.

Figure 4:
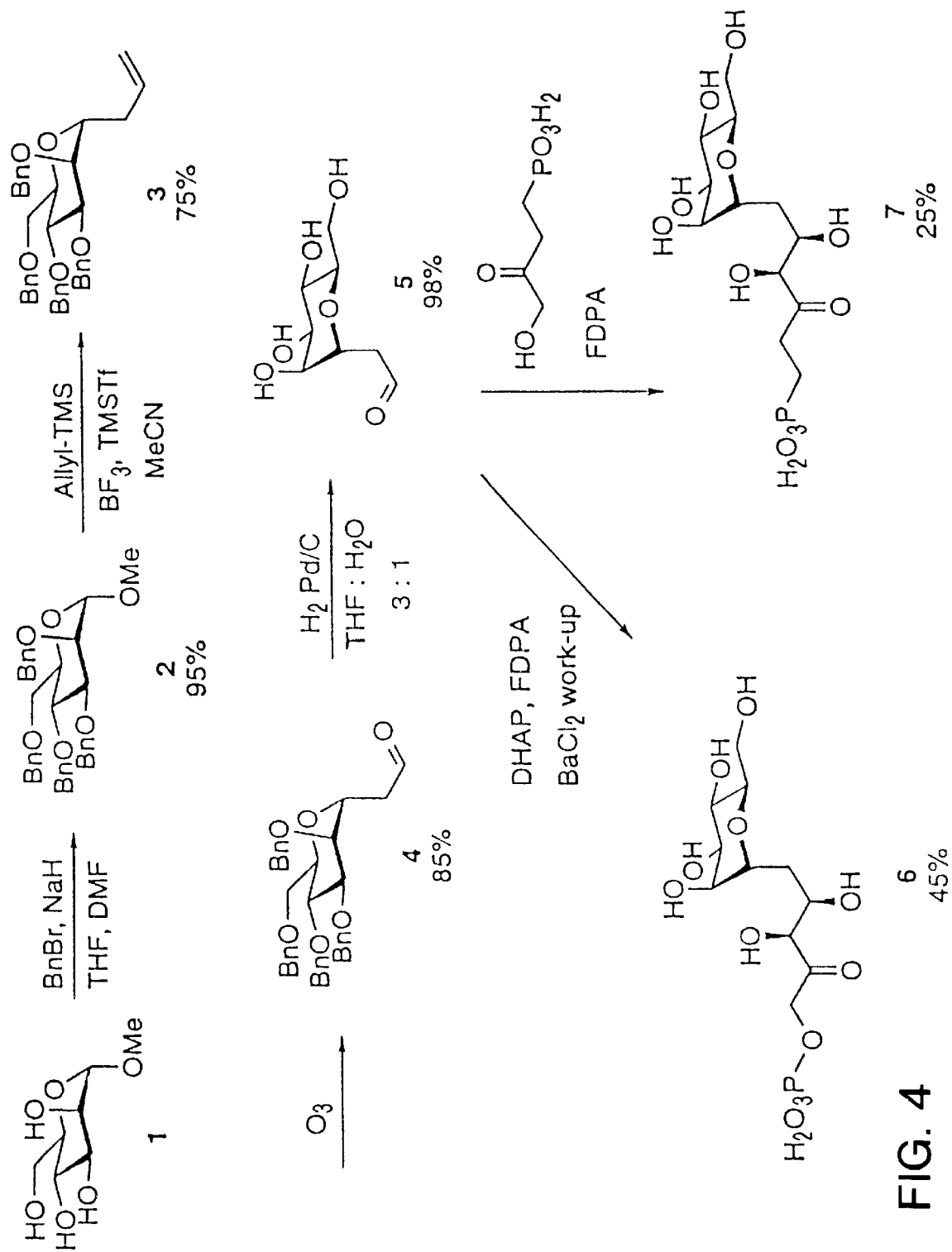
FIG. 4 illustrates the chemoenzymatic synthesis of the C-glycoside phosphate inhibitor 6 using DHAP and FDPA aldolase, and the C-glycoside phosphonate inhibitor 7 using FDPA aldolase and a phosphonate derivative of DHAP—both compounds were derived from D-mannose.

The synthesis of 6 is shown in FIG. 4. D-Mannose methyl glycoside was perbenzylated, followed by allylation to form the C-allyl-perbenzylated intermediate 3. Intermediate 3 was converted to a C-glycoside aldehyde via ozynolysis followed by hydrogenation over Pd/C in THF:$H_2O$ to form the unprotected C-glycoside aldehyde 5. Aldehyde 5 was then coupled with dihydroxyacetone phosphate (DHAP) with FDPA aldolase to provide the syn configurated selectin inhibitor 6.

Compound 7 was achieved using the same coupling procedure of inhibitor 6 with the use of a DHAP phosphonate analog in lieu of DHAP. Both compounds 6 and 7 and other key intermediates were characterized by $^1$H NMR and high resolution mass analysis. Compound 13 (FIG. 5) was synthesized from D-glucose using the same methods as that of compound 6.

Figure 1:
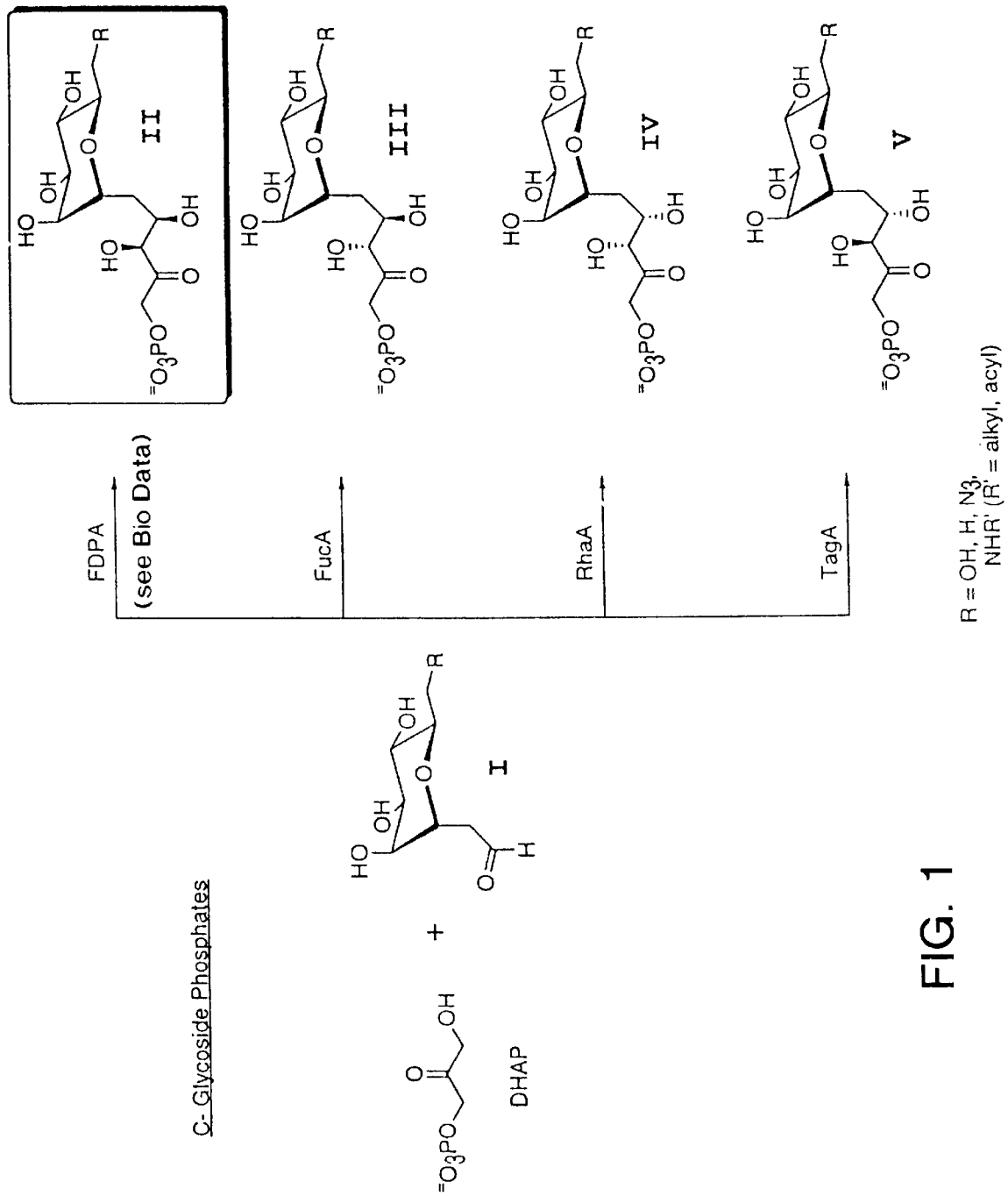
FIG. 1 illustrates various E-, P-, and L- selectin inhibitors (classes II–V) which cover C-glycoside phosphates. Depicted are the substrates and products which include a D-mannose template aldehyde, DHAP, and the indicated aldolases used for the aldolase addition. The various aldolases can be used to provide different configurations at the α and β hydroxyl positions of the product inhibitor. The boxed compound wherein R =OH, represents compound 6 which has been tested with activity as indicated in FIG. 6. R is selected from the group consisting of OH, H, $N_3$, $OSO_3^{2-}$, $OCOCH_2CH_2CONHCH(CH_2CO_2H)CO_2H$, NHR' (R'= alkyl, acyl, decanoyl, phenylacetyl, $COCH_2CH_2CO_2H$).

Analysis of compound 6 (class II compound; FIG. 1) as an inhibitor of $SLe^x$ glycoconjugate binding to E-selectin provides an $IC_{50}$ value of 0.8 mM, according to the method of S. A. DeFrees, et al., viz. J. Am. Chem. Soc. 1995, 117, 66. Since compound 6 has almost the same biological activity as $SLe^x$ (0.50 mM), it can be presumed that all the functional groups required for E-selectin binding in $SLe^x$ therefore exist in 6.

This compound has also been tested against P and L-Selectins and displays excellent activity of >80% inhibition @ 3 mM for both P and L- selectins which is enhanced inhibition activity-better or equal to that of sialyl lewis X.

The synthesis, and physical characterization, of other exemplary compounds of this genus of E-, P-, and L-selectin inhibitors, incorporating phosphates or phosphonate moieties and various stereoconfigurations of the two OH groups which mimic the 4- and 6-OH groups of the Gal residue of the sialic acid residue, are provided below.

Assay for the Biological Activity of $SLe^x$ Mimetics

A soluble form of E-selectin (sol-E-selectin) was prepared for inhibition assays of the $SLe^x$ Mimetics. A 1.67 kbp DNA fragment encoding a truncated structural gene for E-selectin was isolated by PCR amplification of CDNA derived from messenger RNA that was isolated from IL-1 activated human endothelial cells. The CDNA was subcloned into the vector pBluescript II and was transfected into 293 cells. The clones were screened for the production of sol-E-selectin, and the clone 293#3 was selected as the stable cell line that produced the greatest amount of sol-E-selectin per cell. Sol-E-selectin was produced on a large scale from this line using a Nunc cell factory. Recombinant sol-E-selectin was isolated from the media using immunoaffinity chromatography.

The $SLe^x$ Mimetics were assayed for ability to block the adhesion of HL-60 cells to immobilized sol-E-selectins (either on a polymeric column solid support or onto the surface of the assay vessle). Immobilized E-selectin was incubated first with inhibitor and then with HL-60 cells. The bound cells were lysed, and myeloperoxidase released from the bound cells was detected with o-phenylenediamine and hydrogen peroxide. The percentage inhibition was determined by comparing the absorbance of the resulting solution at 492 nm to that in wells containing no inhibitor.

Each data point in the E-selectin assay is a direct measure of cells bound using a quantitative enzyme assay. The values were then plotted to give the titration curve and $IC_{50}$ values. On average, five assays were performed for each inhibitor, and the results were highly reproducible. The standard deviation did not exceed 6.3% for any data point. The $IC_{50}$ values reported here is derived from all the data. Procedure described herein is adopted from Wong et. al. J. Am. Chem. Soc. 1995, 177, 66–79.

EXPERIMENTAL PROTOCOLS

General

A Bruker AMX-400 spectrometer was used for 400 MHz $^1$H NMR and 100 MHz $^{13}$C NMR spectra. High resolution mass spectra (HRMS) were obtained on a VG ZAB-ZSE Mass Spectrometer in fast atom bombardment. For the MS of the compounds that are obtained from the MCC, normal molecular ion peaks (M+H$^+$, M+Na$^+$ or M+Cs$^+$) were recorded without high resolution.

Synthesis of Compound 2 (FIG. 4)

Tetrabenzyl methyl α-D-mannopyranoside. To a solution of methyl α-D-mannopyranoside (1.96g, 9.61 mmol; Aldrich, Sigma), BnBr (8 mL, 67.3 mmol; benzyl bromide), and TBAI (177 mg, 048 mmol; tetrabutylammonium iodide; Aldrich) in THF (20 mL; tetrahydrofuran) at 0° C. was added NaH (2.35 g, 57.6 mmol). The cooling bath was removed and the reaction mixture was allowed to stir for 24 h. The reaction was diluted with EtOAc (50 mL; ethyl acetate) and poured into a saturated $NH_4Cl$ solution (50 mL). The aqueous phase was extracted with EtOAc (2×30 mL) and the combined organic phases were dried ($MgSO_4$) and concentrated under reduced pressure providing the crude oil. Purification by silica gel flash chromatography (hexane:EtOAc, 100% to 9:1 to 1:1) gave the desired product in excellent yield (5.0 g, 92%).

Synthesis of Compound 3 (FIG. 4)

Tetrabenzyl C-allylmannose. To a solution of tetrabenzyl methyl α-D-mannopyranoside 2, (1.0 g, 2.56 mmol; vida supra), at 0° C. was added allyltrimethylsilane (1.22 mL, 7.69 mmol) followed by $BF_3 \cdot Et_2O$ (1.5 mL, 12.8 mmol). The reaction mixture was allowed to warm to 23° C. and TMSOTf (100 mL; trimethylsilyltriflate; Aldrich) was added and the solution was stirred for 24 h. The mixture was poured into a saturated $NaHCO_3$ solution (50 mL) and the organic phase was diluted with $CH_2Cl_2$ (50 mL). The aqueous phase was extracted with $CH_2Cl_2$ (2×25 mL) and the combined organic phases were dried ($MgSO_4$), filtered, and concentrated under reduced pressure. The crude oil was purified by silica gel flash chromatography ($CH_2Cl_2$/ MeOH, 9:1) giving compound 3 as a single α-anomer in good yield (397 mg, 76%).

Synthesis of Compound 4 (FIG. 4)

Perbenzyl aldehyde. To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual $O_3$, pure $O_2$ was bubbled through until the solution turned clear. DMS (1.7 mL, 24.0 mmol; dimethylsulfide) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) giving the perbenzyl aldehyde, compound 4 in good yield.

Synthesis of Compound 5 (FIG. 4)

Hydrogenation of perbenzyl aldehyde 4 to D-Mannose C-glycoside aldehyde 5. 2 mmol (1132 mg) of compound 4 is dissolved in a mixture of tetrahydrofuran and water (3:1) and hydrogenated at 1 atmosphere in presence of a catalytic amount of Pd/C (Aldrich; 10% Pd/C). The mixture is allowed to react overnight and the catalyst is filtered off using a celite pad. The solvent is evaporated under vacuum and the product 5 is isolated (440 mg, 98%) as a mixture of aldehyde and dihydrate as revealed by its $^1$H-NMR and $^{13}$C-NMR (∂, ppm); data provided in FIGS. 9–10.

Synthesis of Compound 6 (FIG. 4)

Enzymatic coupling of aldehyde 5 and DHAP. 1.2 mmol (270 mg) of aldehyde 5 are dissolved in DHAP (1 mmol, 3.2 mL of a 314 mM solution; dihydroxyacetone phosphate; Sigma, Fluka, etc). The pH is adjusted to 6.8 by adding NaOH and 400 u of FDP aldolase (Sigma) are added. The progress of the reaction is followed by DHAP consumption (UV assay). After overnight period >90% of the DHAP had been consumed. The pH is adjusted to 7.5 and 1 g of $BaCl_2 \cdot 2H_2O$ (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 $H^+$ until the solid is completely dissolved (≈30 min), and the resin is filtered off. The pH of the filtrate is adjusted to 7.0 by adding NaOH. Liophylization yields 189 mg (45%) of the C-glycosyl phosphate 6 as sodium salt. NMR data are provided in FIGS. 9–10.

Synthesis of Compound 7 (FIG. 4)

Enzymatic coupling of aldehyde 5 and C-DHAP (3-keto-4-hydroxy-butanyl-1-phosphonate; reagent is synthesized and characterized by Fessner et al. *Angew. Chem. Int. Ed. Eng.*, 1994, 33, 209; Arth et al. *Liebigs Ann*, 1995, 2037): 1.2 mmol (270 mg) of aldehyde 5 are dissolved in C-DHAP (1mmol, 3 mL of a 330 mM solution). The pH is adjusted to 6.7 by adding NaOH and 1500 u of FDP aldolase (Sigma) are added. The progress of the reaction is followed by C-DHAP consumption (UV assay) and by $^{31}P$-NMR spectroscopy. After 1 week >80% of the C-DHAP had been consumed and $^{31}P$-Nmr showed the appearance of new products, one of them being major in the mixture. The pH is adjusted to 8 and 1 g of $BaCl_2 \cdot 2H_2O$ (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 $H^+$ until the solid is completely dissolved (≈30 min), and the resin is filtered off. The pH of the filtrate is adjusted to 7.0 by adding NaOH. Liophylization yields a mixture of phosphonates that are further separated by ion exchange ($HCO_3^-$ column, 400 mM of $Et_3NH \cdot HCO_3$), converted to the $H^+$ form (Dowex 50 $H^+$) and liophylized to yield 104 mg (25%) of 7 as sodium salt. NMR data are provided in FIGS. 9–10.

Figure 5:
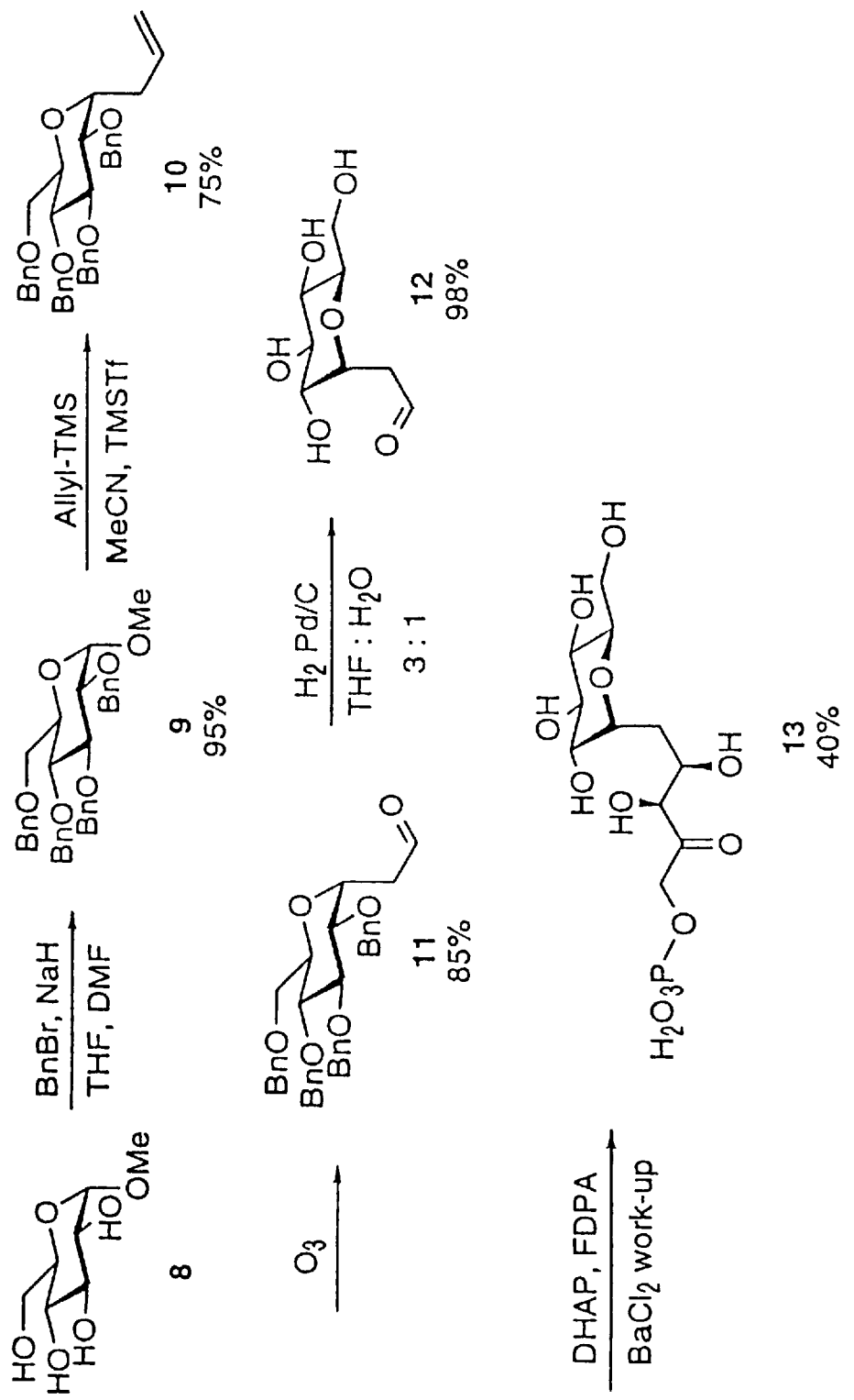
FIG. 5 illustrates the chemoenzymatic synthesis of the D-glucose based C-glycoside phosphate inhibitor 13 using DHAP and FDPA aldolase.
Figure 6:
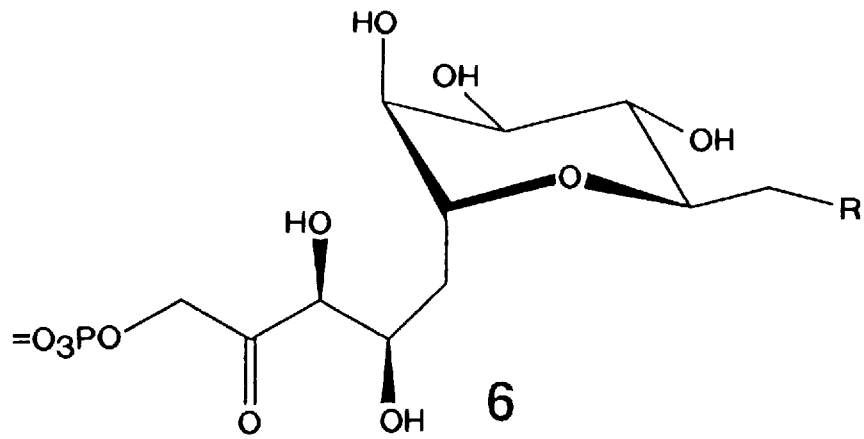
FIG. 6 illustrates activity data for compound 6 ($IC_{50}$ =0.8 mM. Compound 6 has almost the same biological activity as $SLe^x$ (0.50 mM). This compound has also been tested against P and L- Selectins and displays excellent activity of >80% inhibition @ 3 mM for both P and L- selectins which is enhanced inhibition activity-better or equal to that of sialyl lewis X.

Synthesis of Compound 9 (FIG. 5)

Tetrabenzyl methyl α-D-glucopyranoside. To a solution of methyl α-D-glucopyranoside (1.96 g, 9.61 mmol; Aldrich, Sigma), BnBr (8 mL, 67.3 mmol; benzyl bromide), and TBAI (177 mg, 048 mmol; tetrabutylammonium iodide; Aldrich) in THF (20 mL; tetrahydrofuran) at 0° C. was added NaH (2.35 g, 57.6 mmol). The cooling bath was removed and the reaction mixture was allowed to stir for 24 h. The reaction was diluted with EtOAc (50 mL; ethyl acetate) and poured into a saturated $NH_4Cl$ solution (50 mL). The aqueous phase was extracted with EtOAc (2×30 mL) and the combined organic phases were dried ($MgSO_4$) and concentrated under reduced pressure providing the crude oil. Purification by silica gel flash chromatography (hexane:EtOAc, 100% to 9:1 to 1:1) gave the desired product in excellent yield (5.0 g, 92%).

Synthesis of Compound 10 (FIG. 5)

Tetrabenzyl C-allylglucose. To a solution of tetrabenzyl methyl α-D-glucopyranoside 9, (1.0 g, 2.56 mmol; vida supra), at 0° C. was added allyltrimethylsilane (1.22 mL, 7.69 mmol) followed by $BF_3 \cdot Et_2O$ (1.5 mL, 12.8 mmol). The reaction mixture was allowed to warm to 23° C. and TMSOTf (100 mL; trimethylsilyltriflate; Aldrich) was added and the solution was stirred for 24 h. The mixture was poured into a saturated $NaHCO_3$ solution (50 mL) and the organic phase was diluted with $CH_2Cl_2$ (50 mL). The aqueous phase was extracted with $CH_2Cl_2$ (2×25 mL) and the combined organic phases were dried ($MgSO_4$), filtered, and concentrated under reduced pressure. The crude oil was purified by silica gel flash chromatography ($CH_2Cl_2$/MeOH, 9:1) giving compound 10 as a single α-anomer in good yield (397 mg, 76%).

Synthesis of Compound 11 (FIG. 5)

Perbenzyl aldehyde. To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual 03, pure 02 was bubbled through until the solution turned clear. DMS (1.7 mL, 24.0 mmol; dimethylsulfide) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) giving the perbenzyl aldehyde, compound 11 in good yield.

Synthesis of Compound 12 (FIG. 5)

Hydrogenation of perbenzyl aldehyde 11 to D-Glucose C-glycoside aldehyde 12. 2 mmol (1132 mg) of compound 11 is dissolved in a mixture of tetrahydrofuran and water (3:1) and hydrogenated at 1 atm in presence of a catalytic amount of Pd/C. The mixture is allowed to react overnight and the catalyst is filtered off using a celite pad. The solvent is evaporated under vacuum and the product 12 is isolated (442 mg, 98%) as a mixture of aldehyde and hemicacetal with the hydroxyl at C-2 as revealed by its spectral data. $^1H$-NMR ($\partial$, ppm) and $^{13}C$-NMR ($\partial$, ppm) data are provided in FIGS. 9–10.

Synthesis of Compound 13 (FIG. 5)

Enzymatic coupling of aldehyde 12 and DHAP. 1.2 mmol (270 mg) of aldehyde 5 are dissolved in DHAP (1mmol, 3.2 mL of a 314 mM solution; Aldrich/Sigma). The pH is adjusted to 6.8 by adding NaOH and 400 u of FDP aldolase (Sigma) are added. The progress of the reaction is followed by DHAP consumption (UV assay). After overnight period >90% of the DHAP had been consumed. The pH is adjusted to 7.5 and 1 g of $BaCl_2 \cdot 2H_2O$ (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 $H^+$ until the solid is completely dissolved (≈30 min), and the resin is filtered off. The pH of the filtrate is adjusted to 7.0 by adding NaOH. Liophylization yields 168 mg (45%) of the C-glycosyl phosphate 13 as sodium salt. $^1H$-NMR ($\partial$, ppm) and $^{13}C$-NMR ($\partial$, ppm) data are provided in FIGS. 9–10.

General Synthesis for type II compounds (as shown in FIG. 1)

Enzymatic coupling of aldehyde class I (wherein R=OH, H, $N_3$, NHR' (R'=alkyl, acyl, etc.) and DHAP (dihydroxyacetone phosphate; Aldrich, Sigma etc). 1.2 mmol of aldehyde I are dissolved in DHAP (1mmol). The pH is adjusted to 6.8 by adding NaOH and 400 u of FDP aldolase (Sigma) are added. The progress of the reaction is followed by DHAP consumption (UV assay). After overnight period >90% of the DHAP is consumed. The pH is adjusted to 7.5 and of BaCl$_2$•2H$_2$O (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 H$^+$ until the solid is completely dissolved ($\approx$30 min), and the resin is filtered off. The pH of the filtrate is adjusted to 7.0 by adding NaOH. Liophylization yields the C-glycosyl phosphate II as sodium salt.

General Synthesis for type III compounds (as shown in FIG. 1)

Enzymatic coupling of aldehyde class I (wherein R is selected from the group consisting of OH, H, N$_3$, OSO$_3^{2-}$, OCOCH$_2$CH$_2$CONHCH(CH$_2$CO$_2$H) CO$_2$H, NHR' (R'= alkyl, acyl, decanoyl, phenylacetyl, COCH$_2$CH$_2$CO$_2$H)) and DHAP (dihydroxyacetone phosphate; Aldrich, Sigma etc). 1.2 mmol of aldehyde I are dissolved in DHAP (1mmol). The pH is adjusted to 6.8 by adding NaOH and 400 u of Fuc aldolase (Sigma) are added. The progress of the reaction is followed by DHAP consumption (UV assay). After overnight period >90% of the DHAP is consumed. The pH is adjusted to 7.5 and of BaCl$_2$•2H$_2$O (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 H$^+$until the solid is completely dissolved ($\approx$30 min), and the resin is filtered off. The pH of the filtrate is adjusted to 7.0 by adding NaOH. Liophylization yields the C-glycosyl phosphate III as sodium salt.

General Synthesis for type IV compounds (as shown in FIG. 1)

Enzymatic coupling of aldehyde class I (wherein R is selected from the group consisting of OH, H, N$_3$, OSO$_3^{2-}$, OCOCH$_2$CH$_2$CONHCH(CH$_2$CO$_2$H) CO$_2$H, NHR' (R'= alkyl, acyl, decanoyl, phenylacetyl, COCH$_2$CH$_2$CO$_2$H)) and DHAP (dihydroxyacetone phosphate; Aldrich, Sigma etc). 1.2 mmol of aldehyde I are dissolved in DHAP (1mmol). The pH is adjusted to 6.8 by adding NaOH and 400 u of Rha aldolase (Sigma) are added. The progress of the reaction is followed by DHAP consumption (UV assay). After overnight period >90% of the DHAP is consumed. The pH is adjusted to 7.5 and of BaCl$_2$•2H$_2$O (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 H$^+$ until the solid is completely dissolved ($\approx$30 min), and the resin is filtered off. The pH of the filtrate is adjusted to 7.0 by adding NaOH. Liophylization yields the C-glycosyl phosphate IV as sodium salt.

General Synthesis for type V compounds (as shown in FIG. 1)

Enzymatic coupling of aldehyde class I (wherein R is selected from the group consisting of OH, H, N$_3$, OSO$_3^{2-}$, OCOCH$_2$CH$_2$CONHCH(CH$_2$CO$_2$H)CO$_2$H, NHR' (R'= alkyl, acyl, decanoyl, phenylacetyl, COCH$_2$CH$_2$CO$_2$H)) and DHAP (dihydroxyacetone phosphate; Aldrich, Sigma etc). 1.2 mmol of aldehyde I are dissolved in DHAP (lmmol). The pH is adjusted to 6.8 by adding NaOH and 400 u of Tag aldolase (Sigma) are added. The progress of the reaction is followed by DHAP consumption (UV assay). After overnight period >90% of the DHAP is consumed. The pH is adjusted to 7.5 and of BaCl$_2$•2H$_2$O (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 H$^+$ until the solid is completely dissolved ($\approx$30 min), and the resin is filtered off. The pH of the filtrate is adjusted to 7.0 by adding NaOH. Liophylization yields the C-glycosyl phosphate V as sodium salt.

Figure 2:
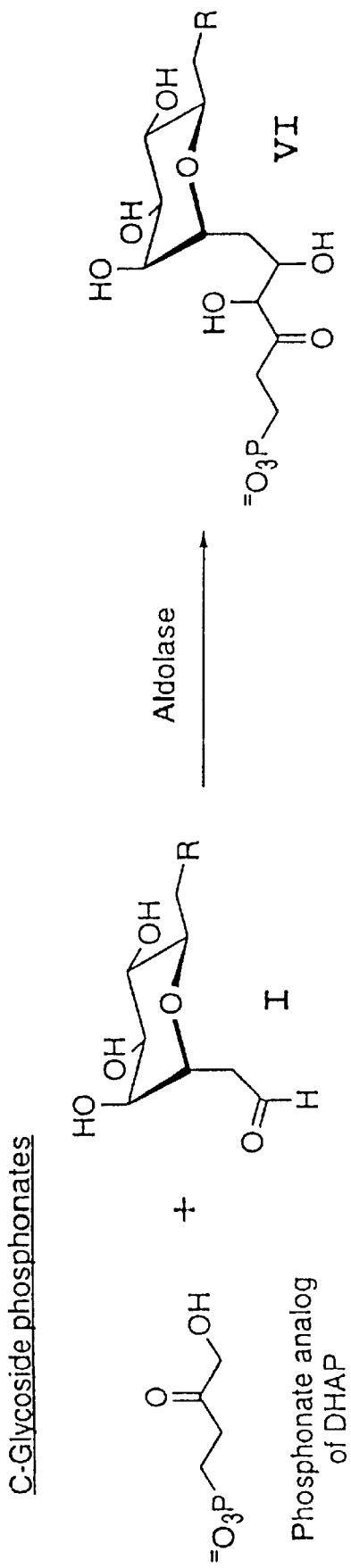
FIG. 2 illustrates various E-, P-, and L- selectin inhibitors (classes VI) which cover C-glycoside phosphonates. Depicted are the substrates and product which include a D-mannose template aldehyde, a phosphonate analog of DHAP, and the desired aldolase used for the aldolase addition. The aldolase can be selected from the group consisting of fructose diphosphate aldolase (FDPA), fucose aldolase (FucA), rhamnose aldolase (RhaA), and tagose aldolase (TagA). The various aldolases can be used to provide different configurations at the α and β hydroxyl positions of the product inhibitor C-glycoside phosphonate (class VI). R is selected from the group consisting of OH, H, $N_3$, $OSO_3^{2-}$, $OCOCH_2CH_2CONHCH(CH_2CO_2H)CO_2H$, NHR' (R'= alkyl, acyl, decanoyl, phenylacetyl, $COCH_2CH_2CO_2H$).

General Synthesis for type VI compounds (as shown in FIG. 2)

Enzymatic coupling of aldehyde class I (wherein R is selected from the group consisting of OH, H, N$_3$, OSO$_3^{2-}$, OCOCH$_2$CH$_2$CONHCH(CH$_2$CO$_2$H)CO$_2$H, NHR' (R'= alkyl, acyl, decanoyl, phenylacetyl, COCH$_2$CH$_2$CO$_2$H)) and C-DHAP (dihydroxyacetone phosphonate derivative (3-keto-4-hydroxy butanyl-1-phosphonate is synthesized and characterized by Fessner et al. *Angew. Chem. Int. Ed. Eng.*, 1994, 33, 209; Arth et al. *Liebgs Ann,* 1995, 2037). 1.2 mmol of aldehyde I are dissolved in the desired DHAP dependent aldolase (1mmol, eg. FDPA, FucA, RhaA, TagA; Sigma) (For a background of DHAP dependent aldolases see Gijsen et al. *Chem. Rev.* 1996, 96, 443). The pH is adjusted to 6.8 by adding NaOH and 400 u of the aldolase are added. The progress of the reaction is followed by DHAP consumption (UV assay). After overnight period >90% of the DHAP is consumed. The pH is adjusted to 7.5 and of BaCl$_2$•2H$_2$O (4.4 mmol) in 5 mL of water is added slowly. The cloudy mixture is kept in an ice bath for 15 min and the precipitates are removed by centrifugation. To the supernatant 2 volumes of acetone are added and the mixture stored at 0° C. for 1 h. The precipitates are collected by centrifugation and the supernatant is discarded. The pellet is treated with Dowex-50 H$^+$ until the solid is completely dissolved ($\approx$30 min), and the resin is filtered off. The pH of the filtrate is adjusted to 7.0 by adding NaOH. Liophylization yields the C-glycosyl phosphate VI as sodium salt.

Figure 7A:
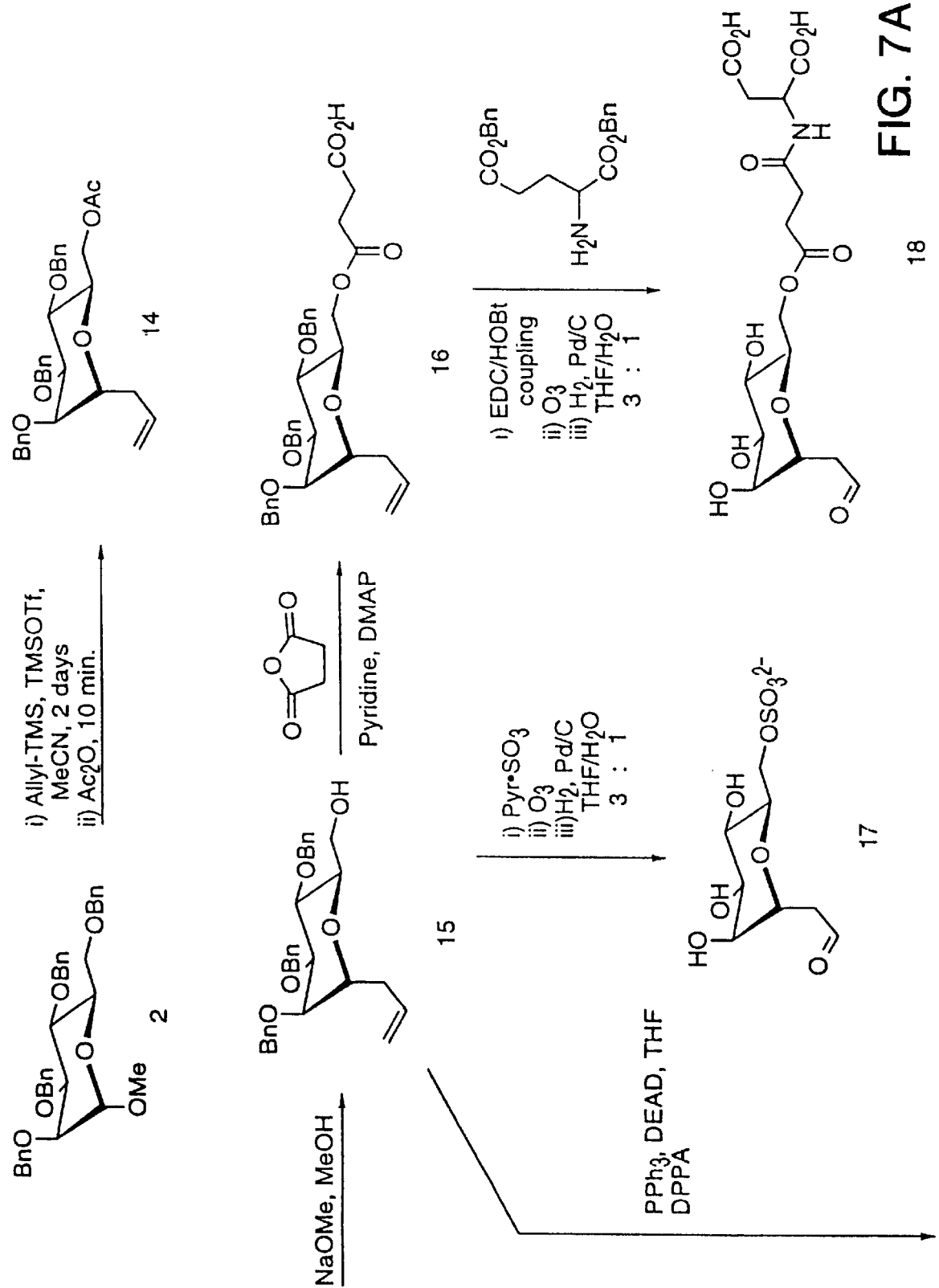
FIGS. 7A and 7B illustrates the synthesis of the key intermediate class I aldehyde as depicted in FIG. 1, used to couple with DHAP or phosphonate analogs of DHAP with aldolase to form the desired inhibitor. The shown intermediate aldehyde products are synthesized by the indicated various chemical routes which share various steps and afford the products 17, 18, 20 and 21.
Figure 7B:
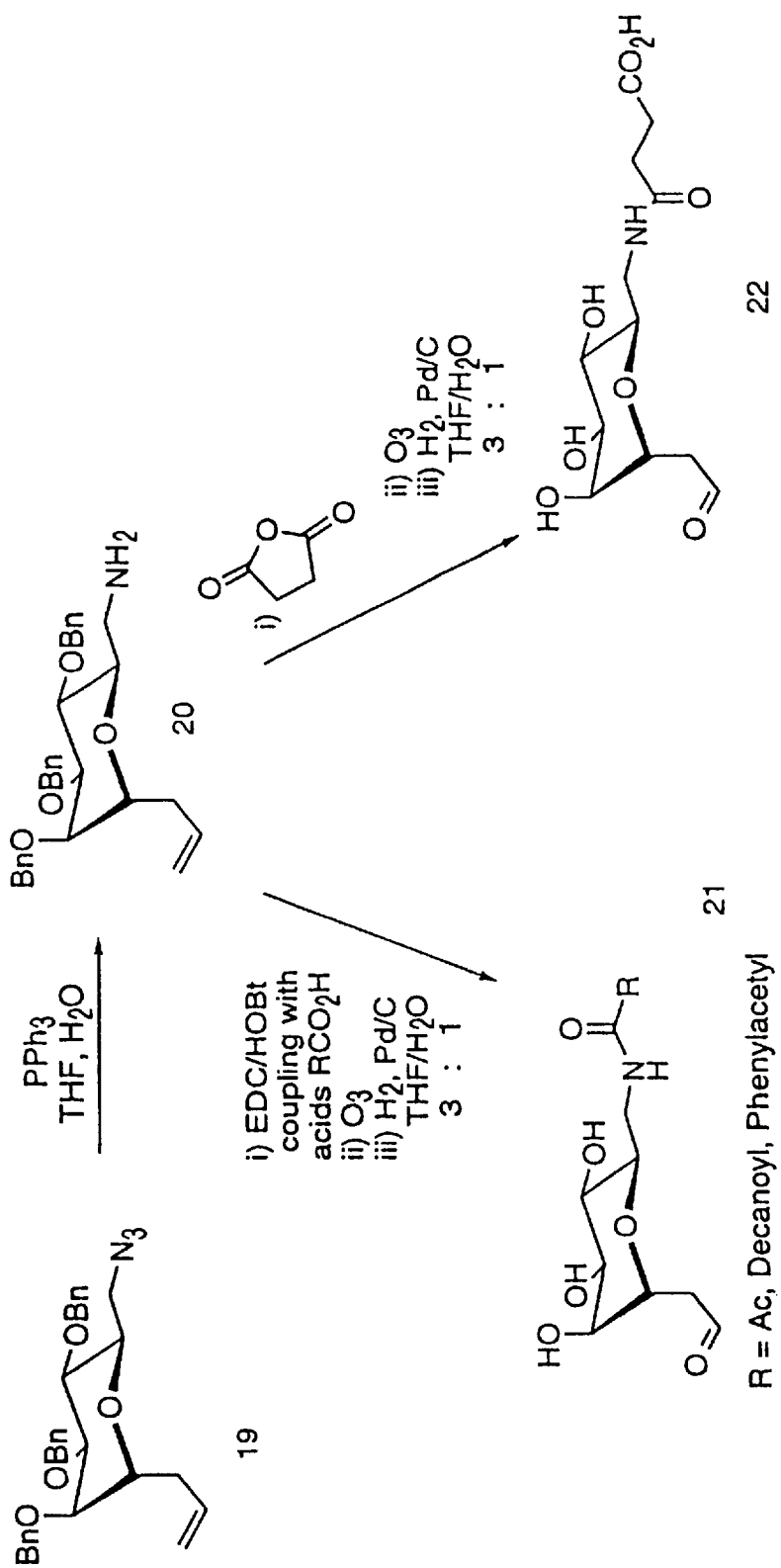

Synthesis of 3-(a-2,3,4-O-tribenzylmannopyranosyl)-1-propene 15 (FIGS. 7A and 7B)

5 mmol of α-Methyl-2,3,4,6-O-Tetra-benzyl-mannopyranoside 2 (vida supra) is dissolved in dry acetonitrile (5 mL, concentration 1.0 Molar) and 2 equivalents of allyl trimethyl silane are added followed by 0.5 eq of TMSOTf under argon. The mixture is allowed to react for 48h and acetic anhydride (2 eq) is added. After 10 min, the reaction is subjected to extractive work-up (ether/water) and purified by chromatography to yield 3.25 mmol (65%) of acetylated product. Deprotection (quantitative yield) is carried out by treatment with NaOMe in MeOH for half an hour and filtration through Dowex-H$^+$.

Synthesis of 3-(α-6-sulphate-mannopyranosyl)-1-propenal 17 (FIGS. 7A and 7B)

Treatment of 15 with 1.2 eq of sulfur trioxide pyridine complex in DMF as solvent, according to Turvey et al. *Advances in Carbohydrate Chemistry and Biochemistry* 1965, 20, 183. Sulphated sugar is then subjected to ozonolysis in MeOH and quenched with DMS. Hydrogenation of the benzyl groups is carried out in THF : H$_2$O mixture under 50 psi of H$_2$ using standard conditions and workup as described supra.

Synthesis of diacid derivative 18 (FIG. 7A and 7B)

Alcohol 15 is treated with 1.1 eq of succinic anhydride in pyridine as solvent and in presence of a catalytic amount of DMAP (4-dimethylaminopyridine). The product so obtained is coupled with dibenzylglutamic acid (Sigma/ Aldrich) using EDC / HOBt coupling system (conditions vida supra). Extractive workup (ether/water) gives the protected precursor, that is subjected to ozonolysis in DCM/MeOH (5:1) quenched by DMS and extracted from ether (conditions vida supra). Hydrogenation of the benzyl groups is carried out in THF : $H_2O$ mixture under 50 psi of $H_2$ to yield product 18 using standard conditions and workup as described supra.

Synthesis of 3-(a-6-azide-2,3,4,tri-O-benzylmannopyranosyl)-1-propenal 19 (FIG. 7)

Compound 15 is subjected to a standard Mitsunobu reaction using triphenylphosphine and diethyl azodicarboxylate with diphenyl phosphoryl azide as nucleophile. Reaction yield after purification by flash chromatography is 80% (Mitsunobu et al. *Synthesis* 1981, 1).

Synthesis of Compound 20 (FIGS. 7A and 7B)

Compound 19 is treated with 1.5 eq of triphenyl phosphine in THF as solvent and in presence of 1.5 eq of water for 3 h at room temperature. Purification is carried out by flash chromatography and the resulting amine is coupled with succinic anhydride (1.1 eq) and triethyl amine (1.1 eq) in MeOH (Uchiyama et al. *Bioorg. & Med. Chem.*, 1996, 4, 1149) to yield 20.

Synthesis of Compound 21 (FIGS. 7A and 7B)

Compound 20 is exposed to EDT / HOBt mediated coupling (conditions vida supra) of the acid selected from the group consistiong of acetic acid, phenylacetic acid and decanoic acid; Aldrich) which is then subjected to ozonolysis in DCM/MeOH (5:1), quenched by DMS and extracted from ether. Hydrogenation of the benzyl groups is carried out in THF $H_2O$ mixture under 50 psi of $H_2$ to yield product 22 as a substrate for the enzymatic coupling using standard workup and reaction conditions, vida supra to form compound 21 (coupling and deprotection procedures as above).

Synthesis of Compound 22 (FIGS. 7A and 7B)

Compound 20 is treated with 1.1 eq of succinic anhydride in pyridine as solvent and in presence of a catalytic amount of DMAP (4-dimethylaminopyridine); conditions and workup are as above. The product so obtained is subjected to ozonolysis in DCM/MeOH (5:1), quenched by DMS and extracted from ether. Hydrogenation of the benzyl groups is carried out in THF : $H_2O$ product under 50 psi of $H_2$ to yield product 22 as a substrate for the enzymatic coupling using standard workup and reaction conditions, vida supra.

Figure 3:
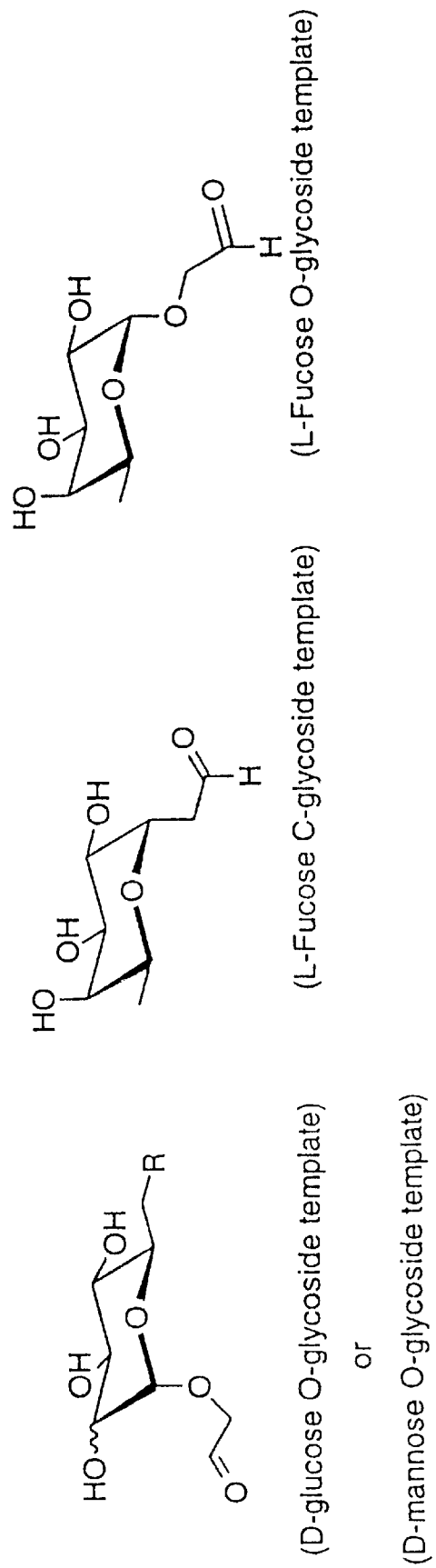
FIG. 3 illustrates other sugar templates which can be used as substrates for the aldolase condensation including O-glycoside- aldehyde derivatives and C-glycoside L-fucose derivatives. R is selected from the group consisting of OH, H, $N_3$, $OSO_3^{2-}$, $OCOCH_2CH_2CONHCH(CH_2CO_2H)CO_2H$, NHR' (R'=alkyl, acyl, decanoyl, phenylacetyl, $COCH_2CH_2CO_2H$).

Synthesis of tribenzyl methyl α-L-fucopyranoside (intermediate to L-fucose C-glycoside template FIG. 3)

To a solution of methyl α-L-fucopyranoside (1.96 g, 9.61 mmol; Aldrich, Sigma), BnBr (8 mL, 67.3 mmol; benzyl bromide), and TBAI (177 mg, 048 mmol; tetrabutylammonium iodide; Aldrich) in THF (20 mL; tetrahydrofuran) at 0° C. was added NaH (2.35 g, 57.6 mmol). The cooling bath was removed and the reaction mixture was allowed to stir for 24 h. The reaction was diluted with EtOAc (50 mL; ethyl acetate) and poured into a saturated $NH_4Cl$ solution (50 mL). The aqueous phase was extracted with EtOAc (2×30 mL) and the combined organic phases were dried ($MgSO_4$) and concentrated under reduced pressure providing the crude oil. Purification by silica gel flash chromatography (hexane:EtOAc, 100% to 9:1 to 1:1) gave the desired product in excellent yield (5.0 g, 92%).

Synthesis of tribenzyl C-allylfucose (intermediate to L-fucose C-glycoside template FIG. 3)

To a solution of tribenzyl methyl α-L-fucopyranoside (1.0 g, 2.56 mmol; vida supra), at 0° C. was added allyltrimethylsilane (1.22 mL, 7.69 mmol) followed by $BF_3 \cdot Et_2O$ (1.5 mL, 12.8 mmol). The reaction mixture was allowed to warm to 23° C. and TMSOTf (100 mL; trimethylsilyltriflate; Aldrich) was added and the solution was stirred for 24 h. The mixture was poured into a saturated $NaHCO_3$ solution (50 mL) and the organic phase was diluted with $CH_2Cl_2$ (50 mL). The aqueous phase was extracted with $CH_2Cl_2$ (2×25 mL) and the combined organic phases were dried ($MgSO_4$), filtered, and concentrated under reduced pressure. The crude oil was purified by silica gel flash chromatography ($CH_2Cl_2$/ MeOH, 9:1) giving the intermediate compound as a single α-anomer in good yield (397 mg, 76%).

Synthesis of perbenzyl aldehyde (intermediate to L-fucose C-glycoside template FIG. 3)

To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual $O_3$, pure $O_2$ was bubbled through until the solution turned clear. DMS (1.7 mL, 24.0 mmol; dimethylsulfide) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) giving the perbenzyl aldehyde in good yield.

Synthesis of L-fucose C-glycoside template as shown in FIG. 3

2 mmol (1132 mg) of above compound is dissolved in a mixture of tetrahydrofuran and water (3:1) and hydrogenated at 1 atmosphere in presence of a catalytic amount of Pd/C (Aldrich; 10% Pd/C). The mixture is allowed to react overnight and the catalyst is filtered off using a celite pad. The solvent is evaporated under vacuum and the product is isolated by standard flash chromatography and workup conditions (vida supra).

Figure 8A:
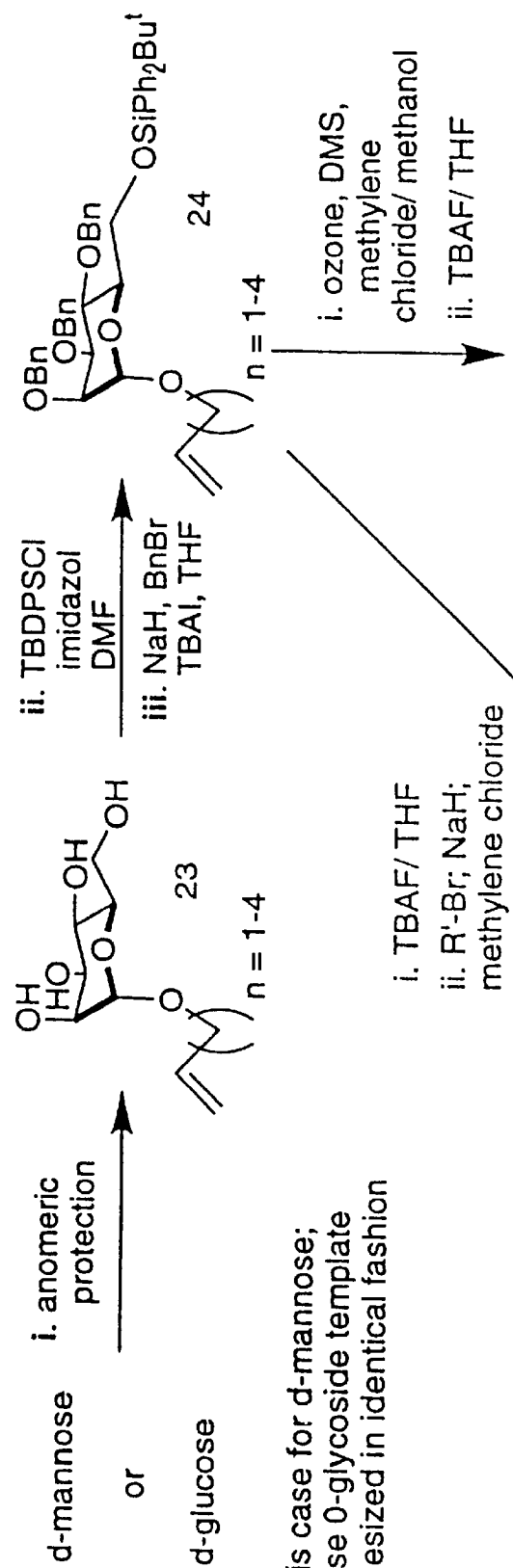
FIG. 8A and 8B illustrates the synthesis of the synthesis of a D-mannose based O-glycide aldehyde.
Figure 8B:
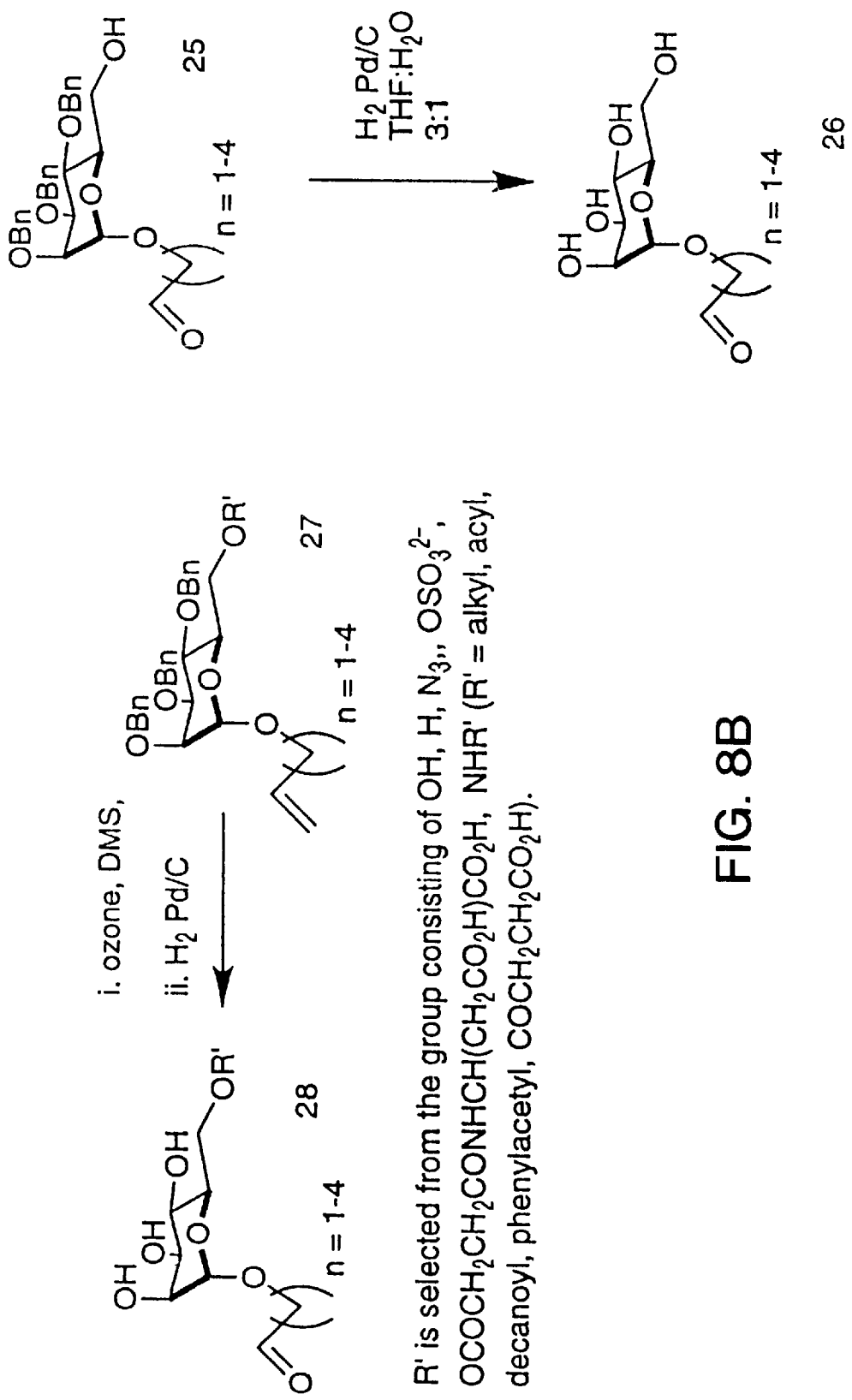

Synthesis of O-glycosyl sugar templates (FIGS. 3 and 8A and 8B)

The use of other sugar templates is illustrated by the following example in which an O-glycosyl sugar is selectively manipulated at C-6. In this particular case a pentenyl glycoside is synthetized, although the method is also applicable to allyl glycosides. The silyl protecting group can be selectively removed by the action of TBAF in THF, releasing the primary hydroxyl group, thus giving the opportunity of carrying out the same kind of chemistry as described above.

Synthesis of compound 23 (FIGS. 8A and 8B)

The O-allyl, O-propenyl, O-butenyl, and O-pentenyl α-(D)-glucoside (23) is prepared according to a literature procedure by Fraser-Reid et al *Syntlett* 1992, 927 wherein the O-methyl α-(D)-glucoside (either glucose or mannose in this case) is stirred in neat solvent (eg. 1.0 Molar propenol (for the O-propenyl derivative), 1.0 Molar allyl alcohol (for the O-allyl derivative), 1.0 Molar butenol (for the O-butenyl derivative) or 1.0 Molar O-pentenol (for the O-pentenyl derivative) at 90° C. for 12 hours. Product is then worked up and purified employing standard conditions vida supra.

Synthesis of compound 24 (FIGS. 8A and 8B)

700 mg (2.8 mmol) of the O-allyl, O-propenyl, O-butenyl, and O-pentenyl α-(D)-glucoside (23) and 420 mg (6.2 mmol) of imidazole are dissolved in 3 ml anhydrous DMF and cooled down to 0° C. The solution is treated dropwise (15 min) with 810 μ(3.1 mmol) of TBDPSCl and the ice bath was removed. After stirring at room temp. for 2 h the reaction was quenched by addition of EtOAc and brine. The aqueous layer was extracted (2×) with EtOAc and the combined organic layers were dried over $Na_2SO_4$, and concentrated. The crude mixture was chromatographed (70 g silica gel, Hex/EtOAc 1:1) to afford 990 mg of a slightly yellow oil. Yield: 2.03 mmol, 73%.

950 mg (1.94 mmol) of the triol are dissolved in 4 ml of anhydrous THF and 36 mg (0.097 mmol) of tetrabutylammonium iodide and 1.15 ml (9.7 mmol) of benzyl bromide were added. To the ice cooled solution 330 mg (95%, 7.8 mmol) of NaH are added at once and the mixture was stirred over night and allowed to warm up to room temp. Under ice cooling the heterogeneous mixture was quenched with sat. $NH_4Cl$ and after diluting with brine the mixture was extracted with ethyl ether (2×, 100 ml). The combined organic layers were dried with $MgSO_4$ and concentrated in vacuo. The crude mixture was chromatographed (100 g silica gel, Hex/$Et_2O$ 10:1) to give 1.044 g of a slightly yellow oil. Yield: 1.34 mmol, 69%.

Synthesis of compound 25 (FIGS. 8A and 8B)

To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual $O_3$, pure $O_2$ was bubbled through until the solution turned clear. DMS (1.7 mL, 24.0 mmol; dimethylsulfide) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) giving the perbenzyl aldehyde. The tert-butyldiphenylsilyl moiety was then removed by adding 1.0 Molar solvent THF (tetrahydrofuran) to the perbenzyl aldehyde followed by the addition of TBAF (tertbutylammonium fluoride Aldrich; 1.0 equivalents; 1.0 M solution). The reaction mixture was stirred for 2 h at 0° C. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) giving the perbenzylated aldehyde 25.

Synthesis of aldehyde 26 (FIGS. 8A and 8B)

Hydrogenation of perbenzyl aldehyde 25 to aldehyde 26. 2 mmol (1132 mg) of compound 25 is dissolved in a mixture of tetrahydrofuran and water (3:1) and hydrogenated at 1 atm in presence of a catalytic amount of Pd/C. The mixture is allowed to react overnight and the catalyst is filtered off using a celite pad. The solvent is evaporated under vacuum and the product 26 is obtained in high yield.

Synthesis of compound 27

The tertbutyldiphenylsilyl moiety was then removed by adding 1.0 Molar solvent THF (tetrahydrofuran) to the perbenzyl aldehyde followed by the addition of TBAF (tertbutylammonium fluoride Aldrich; 1.0 equivalents; 1.0 M solution). The reaction mixture was stirred for 2 h at 0° C. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) to provide the free alcohol. The free alcohol is dissolved in 4 ml of anhydrous methylene chloride and 1.1 equivalents of R'- bromide (chloride or iodide is also acceptable) is added wherein R' is selected from the group consisting of OH, H, $N_3$, $OSO_3^{2-}$, $OCOCH_2CH_2CONHCH$ $(CH_2CO_2H)CO_2H$, NHR' (R'=alkyl, acyl, decanoyl, phenylacetyl, $COCH_2CH_2CO_2H$; Aldrich, Fluka, Sigma) followed by 1.1 equivalents of NaH and the mixture is stirred over night and allowed to warm up to room temp. Under ice cooling the heterogeneous mixture was quenched with sat. $NH_4Cl$ and after diluting with brine the mixture was extracted with ethyl ether (2×100 ml). The combined organic layers were dried with $MgSO_4$ and concentrated in vacuo. The crude mixture was chromatographed by silica gel flash chromatography ($CH_2Cl_2$/ MeOH) to provide the protected olefin.

Synthesis of compound 28

To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual $O_3$, pure $O_2$ was bubbled through until the solution turned clear. DMS (1.7 mL, 24.0 mmol; dimethylsulfide) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil was purified by silica gel flash chromatography ($CH_2Cl_2$/ MeOH) giving the perbenzyl aldehyde. Hydrogenation of perbenzyl aldehyde to provide title aldehyde 28. 2 mmol (1132 mg) of perbenzyl aldehyde is dissolved in a mixture of tetrahydrofuran and water (3:1) and hydrogenated at 1 atm in presence of a catalytic amount of Pd/C. The mixture is allowed to react overnight and the catalyst is filtered off using a celite pad. The solvent is evaporated under vacuum and the product title aldehyde 28.

Synthesis of D-glucose O-glycoside template (as illustrated in FIG. 8

The synthesis of the D-glucose O-glycoside template can be achieved in exactly the same steps as that of D-mannose outlined above for intermediates from 23–28 vida supra.

Synthesis of L-fucose O-glycoside template (as illustrated in FIG. 3) 10 mmol of L-Fucose (Aldrich) are placed in a round-bottom flask together with a large excess of allyl alcohol (Aldrich) and heated to 90° C. Then, 1 eq of boron trifluoride etherate is added dropwise and the mixture is allowed to react overnight. Next, the bulk of allyl alcohol is removed by evaporation in vacuo and the residue is passed through a silica gel column using ethyl acetate:hexane as eluent, first 1:4 to elute the remaining allyl alcohol and then 1:1 to elute the fucose glycoside off the column mainly as α anomer. To a solution of the above prepared terminal olefin (679 mg, 1.20 mmol) in $CH_2Cl_2$:MeOH (8 mL:4 mL) at −78° C. was bubbled $O_3$ in $O_2$ until a blue color persisted. To remove residual $O_3$, pure $O_2$ was bubbled through until the solution turned clear. DMS (1.7 mL, 24.0 mmol; dimethylsulfide) was added and the reaction mixture was warmed to 23° C. and stirred for 24 h. The reaction mixture was evaporated and partitioned between a saturated $NaHCO_3$ solution (50 mL) and EtOAc (5 mL). The aqueous phase was extracted with EtOAc (2×30 mL) and the combined organic phases were dried and concentrated under reduced pressure. The crude oil is purified by silica gel flash chromatography ($CH_2Cl_2$/ MeOH) giving the L-fucose O-glycoside template.

What is claimed is:

1. A method for synthesizing an E-, P- and L- selectin inhibitor represented by the following formula:

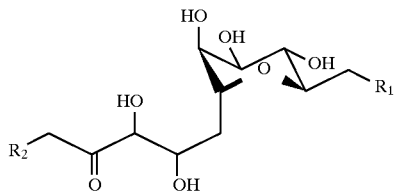

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and —$OPO_3^{2-}$, the method comprising the step of coupling a substrate selected from the group consisting of dihydroxyacetone phosphate (DHPA) or a phosphonate analog thereof with a C-glycoside aldehyde represented by the following formula:

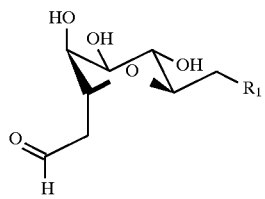

said coupling step being catalyzed by a DHAP dependent aldolase for producing the E-, P- and L- selectin inhibitor.

2. The method as described in claim 1 wherein the substrate is a compound selected from the group consisting of dihydroxyacetone phosphate and 3-keto-4-hydroxy-butanyl-1-phosphonate.

3. The method as described in claim 1 wherein the DHAP dependent aldolase is selected from the group consisting of FDPA, FucA, RhaA and TagA.

4. A method for synthesizing an E-, P- and L- selectin inhibitor represented by the following formula:

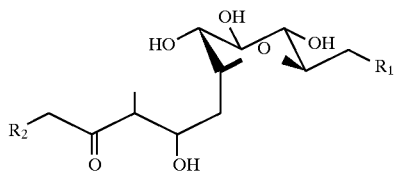

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and —$OPO_3^{2-}$, the method comprising the step of coupling a substrate selected from the group consisting of dehydroxyacetone phosphate (DHPA) or a phosphonate analog thereof with a C-glycoside aldehyde represented by the following formula:

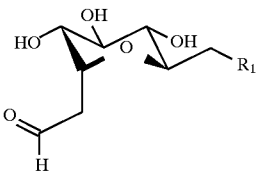

said coupling step being catalyzed by a DHAP dependent aldolase for producing the E-, P- and L- selectin inhibitor.

5. The method as described in claim 4 wherein the substrate is a compound selected from the group consisting of dihydroxyacetone phosphate and 3-keto-4-hydroxy-butanyl-1-phosphonate.

6. The method as described in claim 4 wherein the DHAP dependent aldolase is selected from the group consisting of FDPA, FucA, RhaA and TagA.

7. A method for synthesizing an E-, P- and L- selectin inhibitor represented by the following formula:

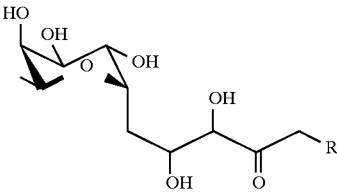

wherein $R_1$ is a radical selected from the group consisting of $CH_2PO_3^{2-}$ and —$OPO_3^{2-}$, the method comprising the step of coupling a substrate selected from the group consisting of dihydroxyacetone phosphate (DHPA) or a phosphonate analog thereof with a C-glycoside aldehyde represented by the following formula:

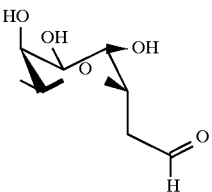

said coupling being catalyzed by a DHAP dependent aldolase for producing the E-, P- and L- selectin inhibitor.

8. The method as described in claim 7 wherein the subtrate is selected from the group consisting of dihydroxy-acetone phosphate and 3-keto-4-hydroxy-butanyl-1-phosphonate.

9. The method as described in claim 7 wherein the DHAP dependent aldolase is selected from the group consisting of FDPA, FucA, RhaA and TagA.

10. A method for synthesizing an E-, P- and L- selectin inhibitor represented by the following formula:

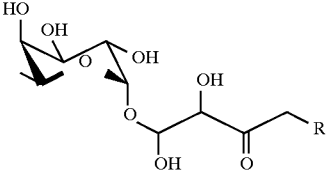

wherein R is a radical selected from the group consisting of —$CH_2PO_3^{2-}$ and —$OPO_3^{2-}$, the method comprising the step of coupling a substrate selected from the group consisting of dihydroxyacetone phosphonate (DHPA) or a phosphonate analog thereof with an 0-glycoside aldehyde represented by the following formula:

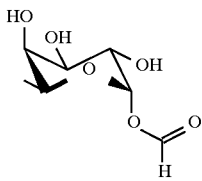

said coupling being catalyzed by a DHAP dependent aldolase for producing the E-, P- and L- selectin inhibitor.

11. The method as described in claim 10 wherein the substrate is selected from the group consisting of dihydroxyacetone phosphate and 3-keto-4-hydroxy-butanyl-1-phosphonate.

12. The method as described in claim 10 wherein the DHAP dependent aldolase is selected from the group consisting of FDPA, FucA, RhaA and TagA.

13. A method for synthesizing an E-, P- and L- selectin inhibitor represented by the following formula:

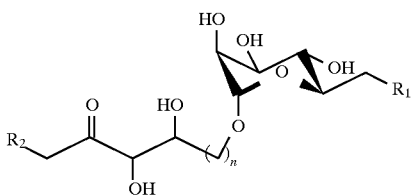

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, wherein n runs from 1 to 4;

the method comprising the step of coupling a substrate selected from the group consisting of dihydroxyacetone phosphate (DHPA) or a phosphonate analog thereof, with a O-glycoside aldehyde with the formula

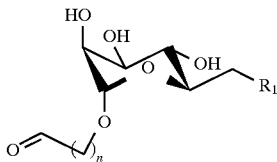

said coupling being catalyzed by a DHAP dependent aldolase for producing the E-, P- and L- selectin inhibitor.

14. The method as described in claim 13 wherein the substrate is selected from the group consisting of dihydroxyacetone phosphate and 3-keto-4-hydroxy-butanyl-1-phosphonate.

15. The method as described in claim 13 wherein the DHAP dependent aldolase is selected from the group consisting of FDPA, FucA, RhaA and TagA.

16. A method for synthesizing an E-, P- and L- selectin inhibitor represented by the following formula:

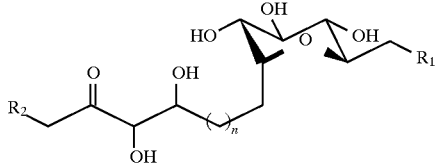

wherein $R_1$ is a radical selected from the group consisting of —H, —OH, $C_1$–$C_6$ , —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, wherein n runs from 1 to 4;

the method comprising the step of coupling a substrate selected from the group consisting of dihydroxyacetone phosphate (DHPA) or a phosphonate analog thereof with a O-glycoside aldehyde with the formula:

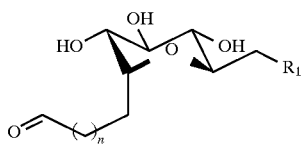

said coupling being catalyzed by a DHAP dependent aldolase for producing the E-, P- and L- selectin inhibitor.

17. The method as described in claim 16 wherein the substrate is selected from the group consisting of dihydroxyacetone phosphate and 3-keto-4-hydroxy-butanyl-1-phosphonate.

18. The method as described in claim 16 wherein the DHAP dependent aldolase is selected from the group consisting of FDPA, FucA, RhaA and TagA.

19. An E-, P- and L- selectin inhibitor represented by the following formula:

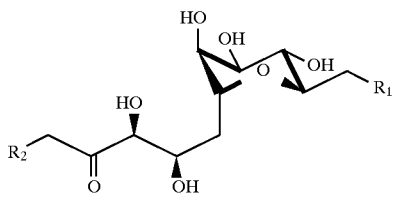

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and $R_2$ is a radical selected from the group consisting of —$CH_2PO_3^{2-}$ and —$OPO_3^{2-}$.

20. An E-, P- and L- selectin inhibitor represented by the following formula:

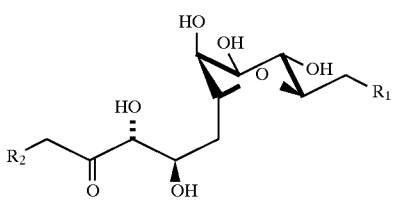

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and —$OPO_3^{2-}$.

21. An E-, P- and L- selectin inhibitor represented by the following formula:

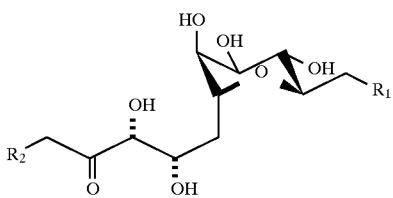

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and $OPO_3^{2-}$.

22. An E-, P- and L- selectin inhibitor represented by the following formula:

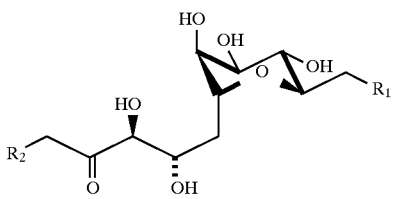

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and —$OPO_3^{2-}$.

23. An E-, P- and L- selectin inhibitor represented by the following formula:

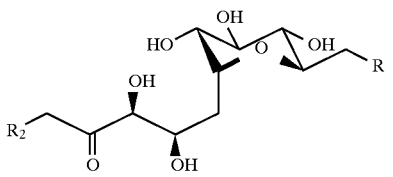

wherein R is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and $R_2$ is a radical selected from the group consisting of —$CH_2PO_3^{2-}$ and —$OPO_3^{2-}$.

24. An E-, P- and L- selectin inhibitor represented by the following formula:

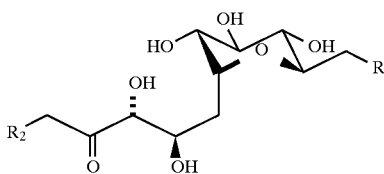

wherein R is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and —$OPO_3^{2-}$.

25. An E-, P- and L- selectin inhibitor represented by the following formula:

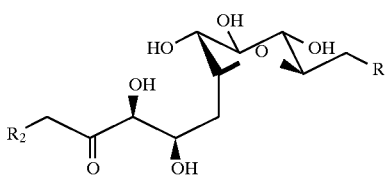

wherein R is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and —$OPO_3^{2-}$.

26. An E-, P- and L- selectin inhibitor represented by the following formula:

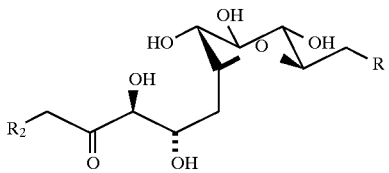

wherein R is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, and wherein $R_2$ is a radical selected from the group consisting of —$CH_2PO_3^{2-}$ and $OPO_3^{2-}$.

27. An E-, P- and L- selectin inhibitor represented by the following formula:

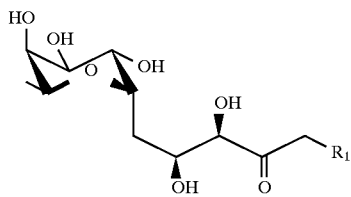

wherein $R_1$ is a radical selected from the group consisting of —$CH_2PO_3^{2-}$ and —$OPO_3^{2}$.

28. An E-, P- and L- selectin inhibitor represented by the following formula:

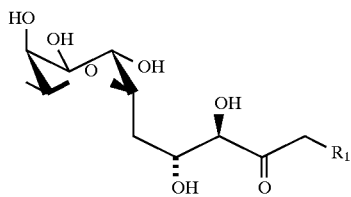

wherein $R_1$ is a radical selected from the group consisting of -$CH_2PO_3^{2-}$.

29. An E-, P- and L- selectin inhibitor represented by the following formula:

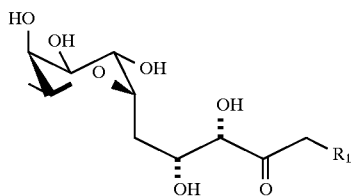

wherein $R_1$ is a radical selected from the group consisting of —$CH_2PO_3^{2-}$ and —$OPO_3^{2-}$.

30. An E-, P- and L- selectin inhibitor represented by the following formula:

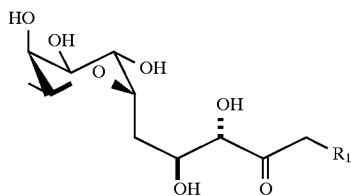

wherein $R_1$ is a radical selected from the group consisting of —$CH_2PO_3^{2-}$ and —$OPO_3^{2-}$.

31. An E-, P- and L- selectin inhibitor represented by the following formula:

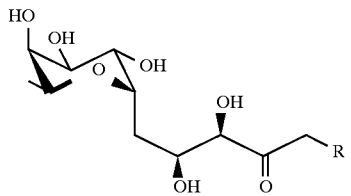

wherein R is a radical selected from the group consisting of —$CH_2PO_3^{2-}$ and —$OPO_3^{2-}$.

32. An E-, P- and L- selectin inhibitor represented by the following formula:

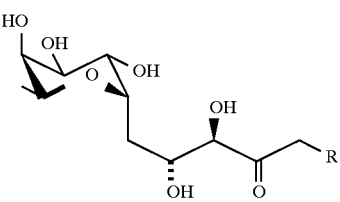

wherein R is a radical selected from the group consisting of —$CH_2PO_3^{2-}$ and —$OPO_3^{2-}$.

33. An E-, P- and L- selectin inhibitor represented by the following formula:

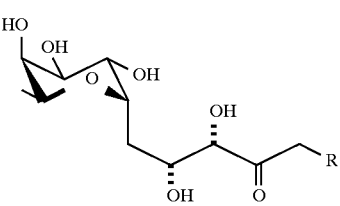

wherein R is a radical selected from the group consisting of —$CH_2PO_3^{2-}$ and —$OPO_3^{2-}$.

34. An E-, P- and L- selectin inhibitor represented by the following formula:

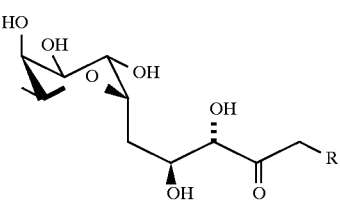

wherein R is a radical selected from the group consisting of —$CH_2PO_3^{2-}$ and —$OPO_3^{2-}$.

35. An E-, P- and L- selectin inhibitor represented by the following formula:

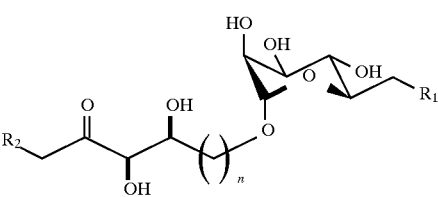

wherein $R_1$ is a radical selected from the group consisting of —H, —OH, $C_1$-$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$-$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2}$, and wherein "n" runs from 1 to 4.

36. An E-, P- and L- selectin inhibitor represented by the following formula:

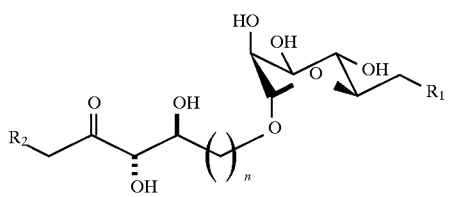

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —$NHR'$, wherein $R'$ is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

37. An E-, P- and L- selectin inhibitor represented by the following formula:

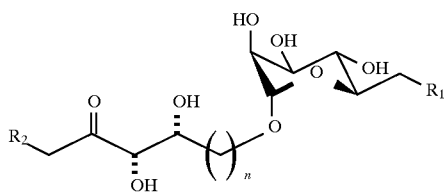

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —$NHR'$, wherein $R'$ is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

38. An E-, P- and L- selectin inhibitor represented by the following formula:

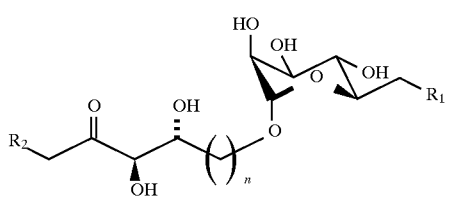

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —$NHR'$, wherein $R'$ is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

39. An E-, P- and L- selectin inhibitor represented by the following formula:

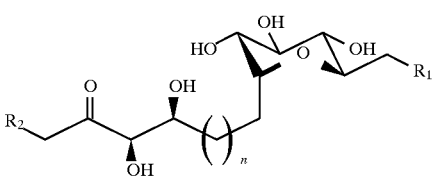

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —$NHR'$, wherein $R'$ is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

40. An E-, P- and L- selectin inhibitor represented by the following formula:

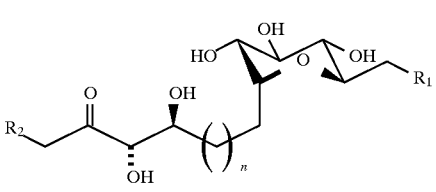

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —$NHR'$, wherein $R'$ is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

41. An E-, P- and L- selectin inhibitor represented by the following formula:

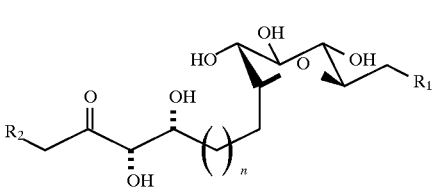

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —$NHR'$, wherein $R'$ is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

42. An E-, P- and L- selectin inhibitor represented by the following formula:

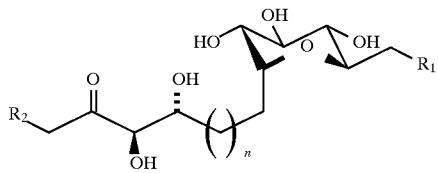

wherein $R_1$ is a radical selected from the group consisting of —H, —OH, $C_1$–$C_6$ —O-alkyl, —OBn, —$N_3$, —$OSO_3^-$, —$OCOCH_2CH_2CONHCH$ ($CH_2CO_2H$) $CO_2H$, and —NHR', wherein R' is a radical selected from the group consisting of $C_1$–$C_6$ alkyl, acyl, decanoyl, phenylacetyl, and —$COCH_2CH_2CO_2H$, wherein $R_2$ is a radical selected from the group consisting of —$CH_2PO_3^{2-}$ and —$OPO_3^{2-}$, and wherein "n" runs from 1 to 4.

* * * * *